(12) United States Patent  
Bottlang et al.

(10) Patent No.: US 8,992,583 B2  
(45) Date of Patent: Mar. 31, 2015

(54) FLEXIBLE PLATE FIXATION OF BONE FRACTURES

(75) Inventors: Michael Bottlang, Portland, OR (US); Steven M. Madey, Portland, OR (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 13/554,119

(22) Filed: Jul. 20, 2012

(65) Prior Publication Data

US 2013/0006310 A1 Jan. 3, 2013

Related U.S. Application Data

(62) Division of application No. 13/166,539, filed on Jun. 22, 2011.

(60) Provisional application No. 61/357,855, filed on Jun. 23, 2010, provisional application No. 61/428,745, filed on Dec. 30, 2010.

(51) Int. Cl.
*A61B 17/80* (2006.01)
*A61B 17/86* (2006.01)

(52) U.S. Cl.
CPC ......... *A61B 17/8085* (2013.01); *A61B 17/8004* (2013.01); *A61B 17/8047* (2013.01); *A61B 17/863* (2013.01)
USPC ............ 606/289; 606/290; 606/291; 606/294

(58) Field of Classification Search
USPC .................................................. 606/289, 291
See application file for complete search history.

(56) References Cited

U.S. PATENT DOCUMENTS

| 2,406,832 A | 9/1946 | Hardinge |
| 2,580,821 A | 1/1952 | Nicola |

(Continued)

FOREIGN PATENT DOCUMENTS

| EP | 0615728 A2 | 9/1994 |
| FR | 742618 A | 3/1933 |

(Continued)

OTHER PUBLICATIONS

"U.S. Appl. No. 13/166,539, Non Final Office Action mailed Jan. 2, 2014", 10 pgs.

(Continued)

*Primary Examiner* — Andrew Yang
*Assistant Examiner* — Olivia C Chang
(74) *Attorney, Agent, or Firm* — Schwegman Lundberg & Woessner, P.A.

(57) ABSTRACT

Embodiments provide methods, apparatuses, and systems for fixation of a fractured bone. In various embodiments, the systems and plates may provide elastic suspension of the receiving holes relative to the osteosynthesis plate. This elastic suspension may promote load distribution between the screws that connect a bone segment to the plate, thereby reducing stress risers and load shielding effect. In addition, stress at the screw holes, and within the construct as a whole, is reduced by incorporation of these elastic elements in the plate. Additionally, in some embodiments, for instance if fracture healing by callus formation is desired, elastic suspension of the receiving holes relative to the osteosynthesis plate may enable small, controlled amounts of relative motion between bone fragments connected by the plate, which may promote fracture healing by callus formation.

12 Claims, 24 Drawing Sheets

(56) References Cited

U.S. PATENT DOCUMENTS

| | | | |
|---|---|---|---|
| 3,807,394 A | 4/1974 | Attenborough | |
| 4,029,091 A * | 6/1977 | von Bezold et al. | 606/33 |
| 4,338,296 A | 7/1982 | Lobmann et al. | |
| 4,361,153 A | 11/1982 | Slocum et al. | |
| 4,743,260 A | 5/1988 | Burton | |
| 4,905,679 A | 3/1990 | Morgan | |
| 4,943,292 A | 7/1990 | Foux | |
| 5,306,310 A | 4/1994 | Siebels | |
| 5,423,816 A | 6/1995 | Lin | |
| 5,468,242 A | 11/1995 | Reisberg | |
| 5,578,036 A | 11/1996 | Stone et al. | |
| 5,681,311 A | 10/1997 | Foley et al. | |
| 5,709,686 A | 1/1998 | Talos et al. | |
| 5,741,258 A | 4/1998 | Klaue et al. | |
| 5,743,913 A | 4/1998 | Wellisz | |
| 5,984,925 A | 11/1999 | Apgar | |
| 6,093,188 A | 7/2000 | Murray | |
| 6,206,882 B1 | 3/2001 | Cohen | |
| 6,340,632 B1 | 1/2002 | Fukada et al. | |
| 6,364,881 B1 | 4/2002 | Apgar et al. | |
| 6,540,746 B1 | 4/2003 | Buhler et al. | |
| 6,663,632 B1 | 12/2003 | Frigg | |
| 6,755,832 B2 | 6/2004 | Happonen et al. | |
| 6,986,771 B2 | 1/2006 | Paul et al. | |
| 6,989,011 B2 | 1/2006 | Paul et al. | |
| 7,048,739 B2 | 5/2006 | Konieczynski et al. | |
| 7,175,624 B2 | 2/2007 | Konieczynski et al. | |
| 7,189,237 B2 | 3/2007 | Huebner | |
| 7,276,070 B2 | 10/2007 | Muckter | |
| 7,341,591 B2 | 3/2008 | Grinberg | |
| 7,377,921 B2 | 5/2008 | Studer et al. | |
| 7,452,370 B2 | 11/2008 | Anderson | |
| 7,572,282 B2 | 8/2009 | Boomer et al. | |
| 7,591,840 B2 | 9/2009 | Suddaby | |
| D603,503 S | 11/2009 | Kriska et al. | |
| D603,504 S | 11/2009 | Kriska et al. | |
| D603,505 S | 11/2009 | Kriska et al. | |
| D603,507 S | 11/2009 | Kriska et al. | |
| D603,508 S | 11/2009 | Kriska et al. | |
| D603,510 S | 11/2009 | Kriska et al. | |
| D603,511 S | 11/2009 | Kriska et al. | |
| D603,961 S | 11/2009 | Kriska et al. | |
| D603,962 S | 11/2009 | Kriska et al. | |
| D603,963 S | 11/2009 | Kriska et al. | |
| D603,964 S | 11/2009 | Kriska et al. | |
| 7,621,942 B2 | 11/2009 | Piehl | |
| 7,641,675 B2 | 1/2010 | Lindemann et al. | |
| 7,651,517 B2 | 1/2010 | Konieczynski et al. | |
| 7,749,257 B2 | 7/2010 | Medoff | |
| 7,806,914 B2 | 10/2010 | Boyd et al. | |
| 7,833,256 B2 | 11/2010 | Biedermann et al. | |
| 7,842,037 B2 | 11/2010 | Schulze | |
| 7,887,569 B2 | 2/2011 | Frigg | |
| 7,887,587 B2 | 2/2011 | Griffiths | |
| 7,914,561 B2 | 3/2011 | Konieczynski et al. | |
| 8,486,070 B2 | 7/2013 | Morgan et al. | |
| 8,687,865 B2 | 4/2014 | Wilson et al. | |
| 8,790,379 B2 | 7/2014 | Madey et al. | |
| 2004/0006343 A1 | 1/2004 | Sevrain | |
| 2004/0019353 A1 | 1/2004 | Freid | |
| 2004/0097937 A1 | 5/2004 | Pike et al. | |
| 2004/0220570 A1 | 11/2004 | Frigg | |
| 2005/0090825 A1 | 4/2005 | Pfefferle et al. | |
| 2005/0096657 A1 | 5/2005 | Autericque et al. | |
| 2005/0116930 A1 | 6/2005 | Gates | |
| 2005/0196421 A1 | 9/2005 | Hunter et al. | |
| 2005/0216008 A1 | 9/2005 | Zwirnmann et al. | |
| 2005/0273105 A1 | 12/2005 | Konieczynski et al. | |
| 2005/0288668 A1 | 12/2005 | Brinkhaus | |
| 2006/0058796 A1 | 3/2006 | Hartdegen et al. | |
| 2006/0116682 A1 | 6/2006 | Longo | |
| 2006/0155282 A1 | 7/2006 | Vese | |
| 2006/0195099 A1 | 8/2006 | Bottlang | |
| 2006/0264949 A1 | 11/2006 | Kohut et al. | |
| 2007/0055251 A1 * | 3/2007 | Huebner et al. | 606/69 |
| 2007/0118127 A1 | 5/2007 | Serhan et al. | |
| 2007/0213729 A1 | 9/2007 | Lindemann et al. | |
| 2008/0027439 A1 | 1/2008 | Sasing | |
| 2008/0147122 A1 | 6/2008 | Jackson | |
| 2008/0147125 A1 | 6/2008 | Colleran et al. | |
| 2008/0200955 A1 | 8/2008 | Tepic | |
| 2008/0275509 A1 | 11/2008 | Clifford et al. | |
| 2008/0306536 A1 | 12/2008 | Frigg | |
| 2009/0036930 A1 | 2/2009 | Allison | |
| 2009/0043341 A1 | 2/2009 | Tyber et al. | |
| 2009/0062915 A1 | 3/2009 | Kohm et al. | |
| 2009/0118768 A1 | 5/2009 | Sixto, Jr. et al. | |
| 2009/0118769 A1 | 5/2009 | Sixto, Jr. et al. | |
| 2009/0118770 A1 | 5/2009 | Sixto, Jr. et al. | |
| 2009/0125067 A1 | 5/2009 | Mazzuca et al. | |
| 2009/0125069 A1 | 5/2009 | Sixto, Jr. et al. | |
| 2009/0125070 A1 | 5/2009 | Sixto, Jr. et al. | |
| 2009/0157121 A1 | 6/2009 | Harris et al. | |
| 2009/0157123 A1 | 6/2009 | Appenzeller et al. | |
| 2009/0222049 A1 | 9/2009 | Frigg et al. | |
| 2009/0234393 A1 | 9/2009 | Sournac et al. | |
| 2009/0270924 A1 | 10/2009 | Wing et al. | |
| 2009/0318921 A1 | 12/2009 | White et al. | |
| 2009/0318976 A1 | 12/2009 | Gabriel et al. | |
| 2010/0010541 A1 | 1/2010 | Boomer et al. | |
| 2010/0036430 A1 | 2/2010 | Hartegen et al. | |
| 2010/0076495 A1 | 3/2010 | Lindemann et al. | |
| 2010/0094351 A1 | 4/2010 | Haggenmaker et al. | |
| 2010/0114177 A1 | 5/2010 | Piehl | |
| 2010/0131012 A1 | 5/2010 | Ralph et al. | |
| 2010/0131013 A1 | 5/2010 | Ralph et al. | |
| 2010/0217327 A1 | 8/2010 | Vancelette et al. | |
| 2010/0249850 A1 | 9/2010 | Cerynik et al. | |
| 2010/0305569 A1 | 12/2010 | Leuenberger et al. | |
| 2011/0118742 A1 | 5/2011 | Hulliger et al. | |
| 2011/0319942 A1 | 12/2011 | Bottlang et al. | |
| 2012/0310289 A1 | 12/2012 | Bottland et al. | |

FOREIGN PATENT DOCUMENTS

| | | |
|---|---|---|
| WO | WO-2011163387 A2 | 12/2011 |
| WO | WO-2013021357 A1 | 2/2013 |

OTHER PUBLICATIONS

"U.S. Appl. No. 13/166,539, Non Final Office Action mailed Jun. 28, 2013", 10 pgs.

"U.S. Appl. No. 13/166,539, Notice of Non-compliant Amendment mailed Feb. 20, 2014", 3 pgs.

"U.S. Appl. No. 13/166,539, Preliminary Amendment filed Jul. 19, 2012", 7 pgs.

"U.S. Appl. No. 13/166,539, Response filed Jan. 28, 2014 to Non Final Office Action mailed Jan. 2, 2014", 3 pgs.

"U.S. Appl. No. 13/166,539, Response filed Jan. 30, 2014 to Non Final Office Action mailed Jan. 2, 2014", 3 pgs.

"U.S. Appl. No. 13/166,539, Response filed May 2, 2014 to Non Final Office Aciton mailed Feb. 20, 2014", !4 pgs.

"U.S. Appl. No. 13/166,539, Response filed May 6, 2013 to Restriction Requirement mailed Mar. 5, 2013", 9 pgs.

"U.S. Appl. No. 13/166,539, Response filed Oct. 28, 2013 to Non Final Office Action mailed Jun. 28, 2013", 10 pgs.

"U.S. Appl. No. 13/166,539, Restriction Requirement mailed Mar. 5, 2013", 6 pgs.

"U.S. Appl. No. 13/490,249, Amendment filed Jan. 28, 2014", 3 pgs.

"U.S. Appl. No. 13/490,249, Non Final Office Action mailed Sep. 19, 2013", 10 pgs.

"U.S. Appl. No. 13/490,249, Notice of Allowance mailed Mar. 27, 2014", 7 pgs.

"U.S. Appl. No. 13/490,249, Response filed Jan. 21, 2014 to Non Final Office Action mailed Sep. 19, 2013", 12 pgs.

"U.S. Appl. No. 13/490,249, Response filed May 7, 2013 to Restriction Requirement mailed Mar. 7, 2013", 11 pgs.

"U.S. Appl. No. 13/490,249, Response filed Sep. 3, 2013 to Restriction Requirement mailed Jul. 2, 2013", 6 pgs.

"U.S. Appl. No. 13/490,249, Restriction Requirement mailed Mar. 7, 2013", 7 pgs.

(56) References Cited

OTHER PUBLICATIONS

"U.S. Appl. No. 13/490,249, Restriction Requirement mailed Jul. 2, 2013", 8 pgs.

"U.S. Appl. No. 13/490,249, Supplemental Amendment filed Jan. 30, 2014", 3 pgs.

"Australian Application Serial No. 2011270934, First Examiner Report mailed Sep. 12, 2013", 4 pgs.

"European Application Serial No. 11798862.6, Office Action mailed Feb. 1, 2013", 2 pgs.

"European Application Serial No. 11798862.6, Response filed Jul. 30, 2013 to Office Action mailed Feb. 1, 2013", 8 pgs.

"International Application Serial No. PCT/US2011/041484, International Preliminary Report on Patentability mailed Jan. 10, 2013", 6 pgs.

"International Application Serial No. PCT/US2011/041484, International Search Report mailed Feb. 17, 2012", 4 pgs.

"International Application Serial No. PCT/US2011/041484, Written Opinion mailed Feb. 17, 2012", 4 pgs.

"U.S. Appl. No. 13/166,539, Final Office Action mailed May 21, 2014", 9 pgs.

"U.S. Appl. No. 13/166,539, Notice of Allowability mailed Oct. 9, 2014", 4 pgs.

"U.S. Appl. No. 13/166,539, Notice of Allowance mailed Aug. 15, 2014", 7 pgs.

"U.S. Appl. No. 13/166,539, Response filed Jul. 21, 2014 to Final Office Action mailed May 21, 2014", 13 pgs.

"U.S. Appl. No. 14/308,286, Preliminary Amendment filed Sep. 17, 2014", 7 pgs.

"U.S. Appl. No. 14/308,314, Preliminary Amendment filed Sep. 17, 2014", 7 pgs.

\* cited by examiner

US 8,992,583 B2

FLEXIBLE PLATE FIXATION OF BONE FRACTURES

RELATED APPLICATIONS

This application is a Divisional of U.S. patent application Ser. No. 13/166,539, filed on Jun. 22, 2011, which claims priority under 35 U.S.C. §119(e) from U.S. Provisional Patent Application Nos. 61/357,855 filed on Jun. 23, 2010, which claims priority under 35 U.S.C. §119(e) from U.S. Provisional Patent application Nos. 61/428,745 filed on Dec. 30, 2010 the subject matter of which is herein incorporated reference.

GOVERNMENT INTEREST

This invention was made with government support under AR061201 award by the National Institutes of Health. The government has certain rights in the invention.

TECHNICAL FIELD

Embodiments herein relate generally to devices for fixation of a fractured bone.

BACKGROUND

Osteosynthesis plates for stabilization of bone fractures typically are applied with bone screws. Traditionally, bone screws compress a plate onto the bone surface to provide stable fixation. More recently, locking plates have been introduced, which typically have threaded receiving holes for positive, angle-stable engagement with the threaded head portion of a locking screw. These locking plates may provide more stable fixation in the ends of weak, osteoporotic bone compared to traditional, non-locking plates.

Clinically, plate osteosynthesis constructs face two principal challenges. First, an osteosynthesis construct may alter the load distribution in bone, which may either cause bone resorption in cases exhibiting load shielding, or bone fracture due to implant-induced stress risers. Second, the high stiffness of a plate osteosynthesis construct may suppress relative displacement between bone fragments, whereby this interfragmentary motion is important to promote the natural cascade of fracture healing by callus formation. Therefore, overly stiff locking plate constructs may delay or prevent fracture healing by callus formation.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

Figure 1A:
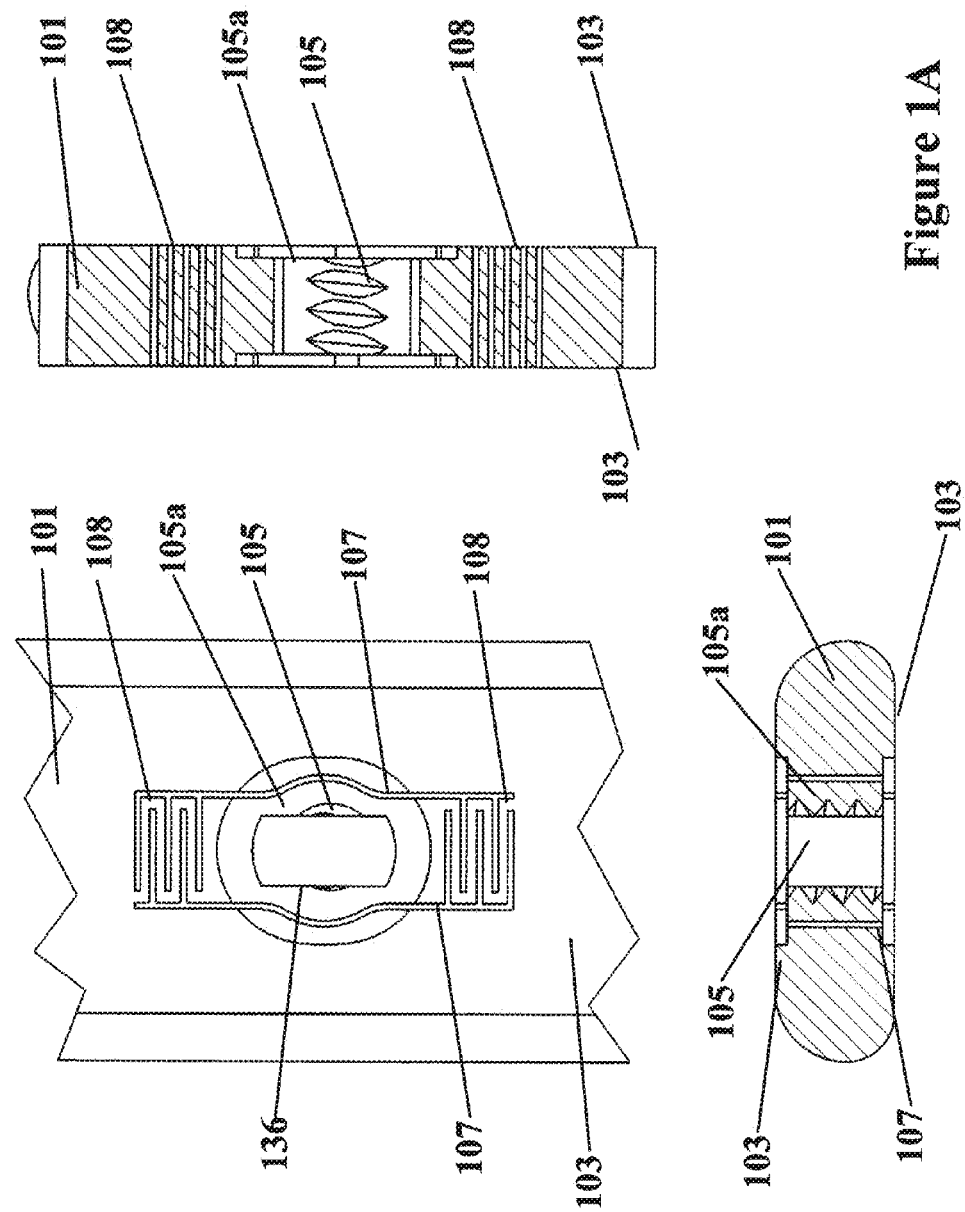
FIG. 1A illustrates a top view, a longitudinal cross-sectional view, and a transverse cross-sectional view of an example of a bone plate having a rivet paired with symmetrically arranged elastic segments and a non-circular, quasi-rectangular through hole, in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, methods, apparatuses, and systems for fixation of a fractured bone are provided. In various embodiments, the systems and plates may provide elastic suspension of receiving holes relative to an osteosynthesis plate. In various embodiments, this elastic suspension may promote load distribution between screws that connect a bone segment to the plate, thereby reducing stress risers and the load shielding effect. In addition, in various embodiments, stress at the screw holes, and within the construct as a whole, may be reduced by incorporation of these elastic elements in the plate. Additionally, in some embodiments, for instance if fracture healing by callus formation is desired, elastic suspension of the receiving holes relative to the osteosynthesis plate may enable small, controlled amounts of relative motion between bone fragments connected by the plate, which may promote fracture healing by callus formation. In some embodiments, relative motion between bone fragments enabled by the elastic elements may be substantially parallel to an upper or lower surface of the bone plate, or substantially parallel to a bone surface.

Unlike other devices, bone plates in accordance with certain embodiments disclosed herein may be configured to be suspended above the surface of the bone, so that a gap is present between the lower surface of the plate and the upper surface of the bone. In various embodiments, this may be accomplished by using locking screws that are designed to engage with a threaded hole in the bone plate. In various embodiments, the coupling of a locking screw with a corresponding portion of a bone plate may ensure that the locking screw is only inserted to a certain extent, for instance the point where the screw locks into the hole of the bone plate. In another embodiment, the receiving hole elements may extend through the lower surface of the bone plate, for instance so that the plate remains suspended over the bone surface even if a bone fastener is used to compress the receiving hole element to the one bone.

In other embodiments, for instance if direct fracture healing is desired, elastic suspension of the receiving holes relative to the osteosynthesis plate may promote elastic compression across a fracture site, whereby the plate may be affixed to the bone with non-locking screws inserted in an eccentric manner in order to induce compression across the fracture. Thus, in various embodiments, it may be beneficial and desirable to stabilize a bone fracture with a plate as disclosed herein to enhance load distribution between screws, to promote fracture site motion when fracture healing by callus formation is desired, and/or to induce prolonged compression across a fracture when direct fracture healing is desired.

Figure 1B:
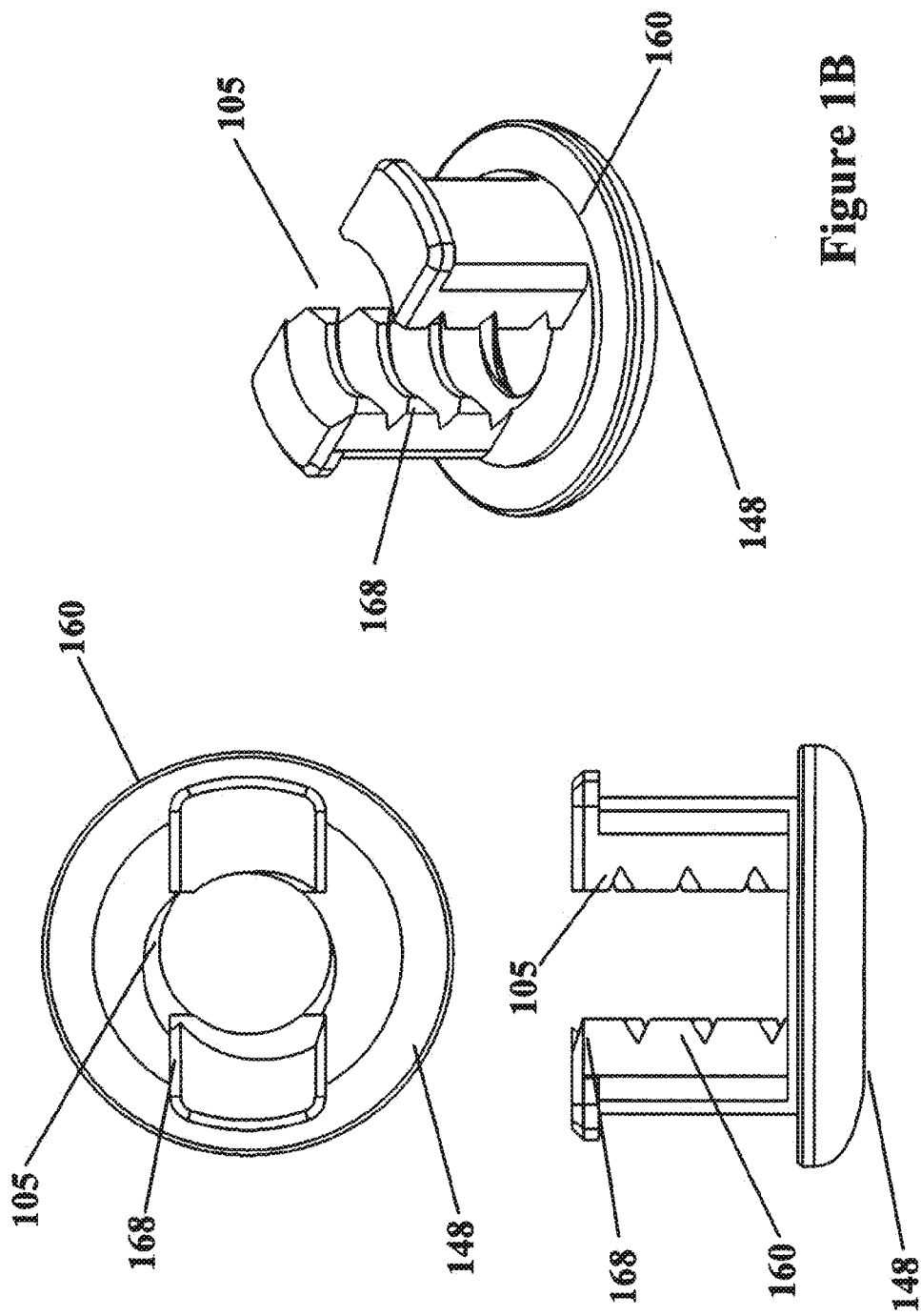
FIG. 1B illustrates bottom, perspective and side views of an example of a rivet for use with the bone plate illustrated in FIG. 1A, wherein the rivet has a generally circular head and a threaded, non-circular expansion portion, in accordance with various embodiments.
Figure 2:
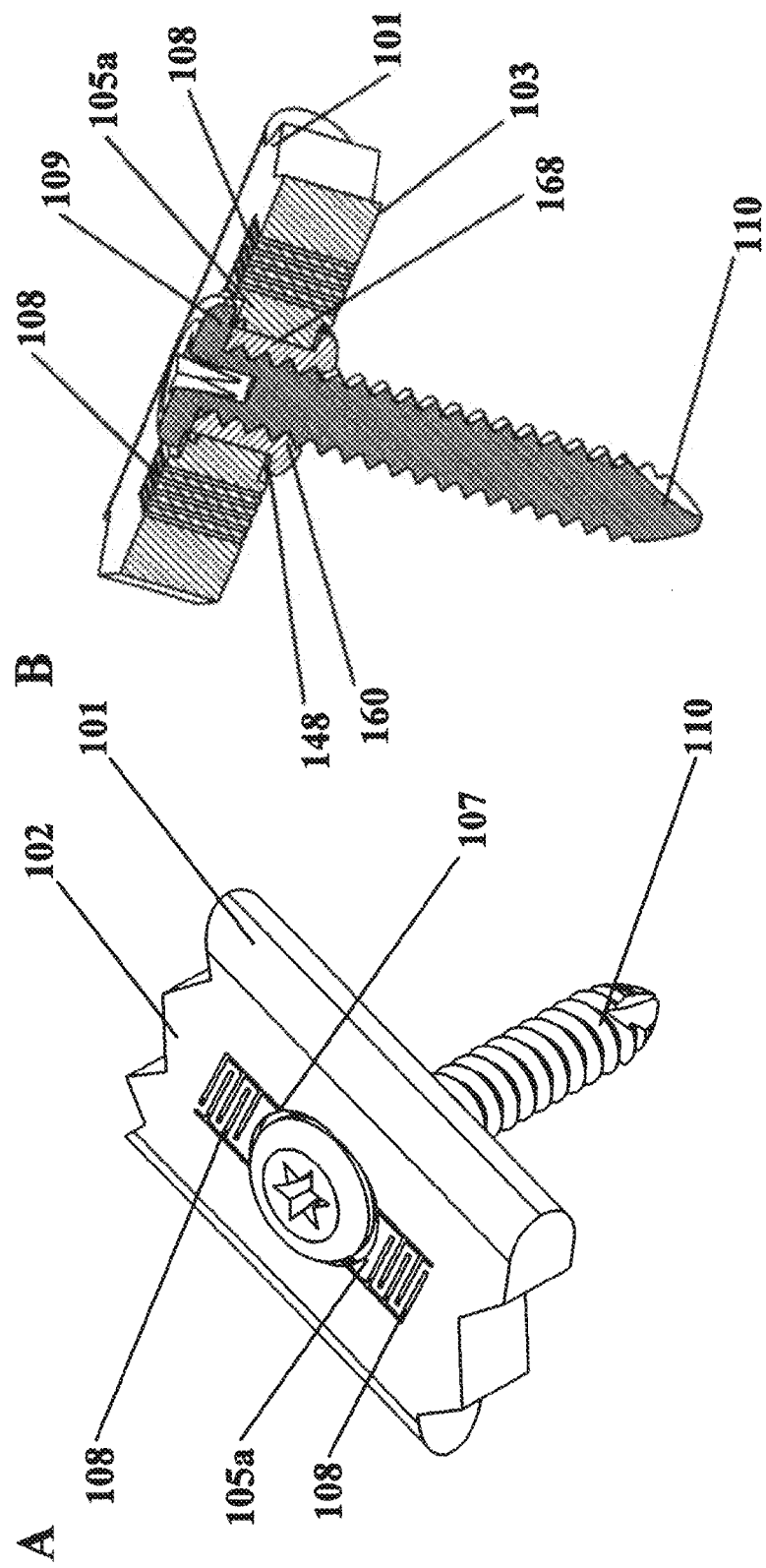
FIG. 2A illustrates a perspective assembly view of a bone plate having a rivet, a locking screw, and a plate section with symmetrically arranged elastic segments, in accordance with various embodiments.
FIG. 2B illustrates a partial perspective assembly view of the bone plate illustrated in FIG. 2A, having a rivet, a locking screw, and a plate section with symmetrically arranged elastic segments, in accordance with various embodiments.
FIG. 2C illustrates a top view of a bone plate having a rectangular rivet, a screw, and a plate section with symmetrically arranged elastic segments flanking the screw receiving hole on either side, in accordance with various embodiments.
FIG. 2D illustrates a cross-sectional view of the bone plate of FIG. 2C, in accordance with various embodiments.
FIG. 2E illustrates an exploded perspective view of the bone plate of FIG. 2C, in accordance with various embodiments.
Figure 2:
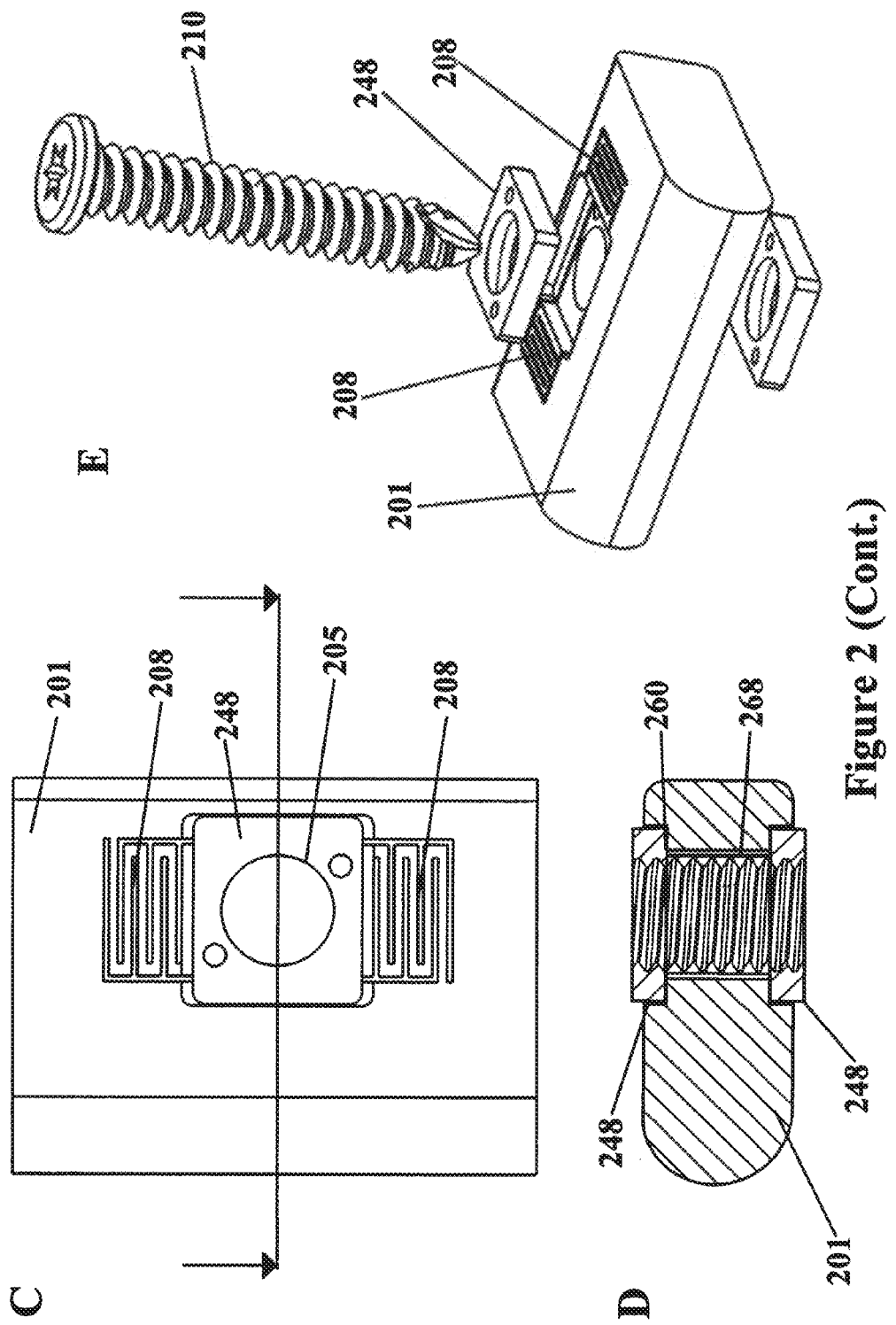

FIG. 1A illustrates a top view, a longitudinal cross-sectional view, and a transverse cross-sectional view of a specific, non-limiting example of a bone plate having a rivet paired with symmetrically arranged elastic segments and a non-circular, quasi-rectangular through hole; FIG. 1B illustrates bottom, perspective and side views of an example of a rivet for use with the bone plate illustrated in FIG. 1A, wherein the rivet has a generally circular head and a threaded, non-circular expansion portion; FIGS. 2A and 2B illustrate a perspective assembly view and a cross-sectional assembly view of a bone plate having a rivet, a locking screw, and a plate section with symmetrically arranged elastic segments, all in accordance with various embodiments. In the example illustrated in FIGS. 1A, 1B, 2A, and 2B, the bone plate 101 may include a rivet 160 with generally symmetrically-arranged elastic segments 108 and a non-circular, quasi-rectangular through hole 136. As illustrated, elastic segments (also referred to herein as elastic elements, elastic beam elements, and spring elements) 108 formed by slots or channels 106 may be generally symmetrically-arranged in proximity of the screw hole 105, for example to enable translation of the screw hole member 105a in a principally axial direction. In various embodiments, screw hole member 105a may include quasi-rectangular through hole 136. In various embodiments, a lower rivet member 160 with a rivet head 148 and a rectangular expansion element 168 may be inserted from the lower plate surface 103 into rectangular through hole 136 of screw hole member 105a. In some embodiments, rivet 160 may be secured in screw hole member 105a by press-fit, whereas in other embodiments, rivet 160 may be secured in screw hole member 105a using a retaining feature that may be adapted to engage with a corresponding receiving feature in quasi-rectangular through hole 136. In various embodiments, rivet head 148 may be sufficiently large to extend laterally across the motion gap 107 of elastic segments 108. In various embodiments, rivet 160 may be configured to protect elastic segments 108 from excessive deformation perpendicular to the plane of plate 101.

In various embodiments, the circular through-hole 105 of rivet 160 may be threaded, and the threads may extend into quasi-rectangular through hole 136 of screw hole member 105a. In various embodiments, a screw 110 with matching threads may be inserted from the upper plate surface 102 through the rivet 160, and the screw locking feature 109 may be sufficiently large to extend laterally across motion gap 107 of elastic segments 108. Thus, in various embodiments, the screw locking feature 109 may therefore limit deflection of screw hole member 105a toward lower plate surface 103. Additionally or alternatively, in some embodiments, the rivet head 148 may limit deflection of screw hole member 105a toward upper plate surface 102. Thus, the illustrated example may enable controlled translation of screw hole member 105a relative to the longitudinal axis of the plate, yet may limit translation relative to the plane of bone plate 101 when screw hole member 105a is guided between the screw locking feature 109 and rivet head 148.

Another example of a bone plate 201 that includes a rivet 260 is shown in FIGS. 2C, 2D, and 2E, which illustrate a top view (FIG. 2C), a cross-sectional view FIG. 2D), and an exploded perspective view (FIG. 2E) of a bone plate having a rectangular rivet 260, a screw 210, and a plate 201 with generally symmetrically arranged elastic segments 208 flanking the screw receiving hole on either side, all in accordance with various embodiments. In this embodiment, rivet 260 may have a rectangular or square shape, and may be recessed into the top and or bottom surfaces of bone plate 201. In some embodiments, rivet 260 may include a separate center shaft portion 268, and one or two shoulder portions 248 coupled thereto. In various embodiments, the upper and/or lower shoulder portions 248 of rivet 260 may limit translation of receiving hole 205 in a direction that is substantially perpendicular to the upper or lower plane of bone plate 201. In other words, rivet 260 may constrain out-of-plane motion, while still allowing axial (e.g., in-plane) translation of receiving hole 205 relative to bone plate 201 (or vice versa). In some embodiments, screw 210 may be a locking screw, for instance, a screw having a threaded head portion, or it may be a non-locking screw. In some embodiments, a non-locking screw may compress shoulder portions 248 and center shaft portion 268 of rivet 260 onto the bone, while plate 201 may retain an axially flexible connection with the bone via elastic segments 208.

Figure 3:
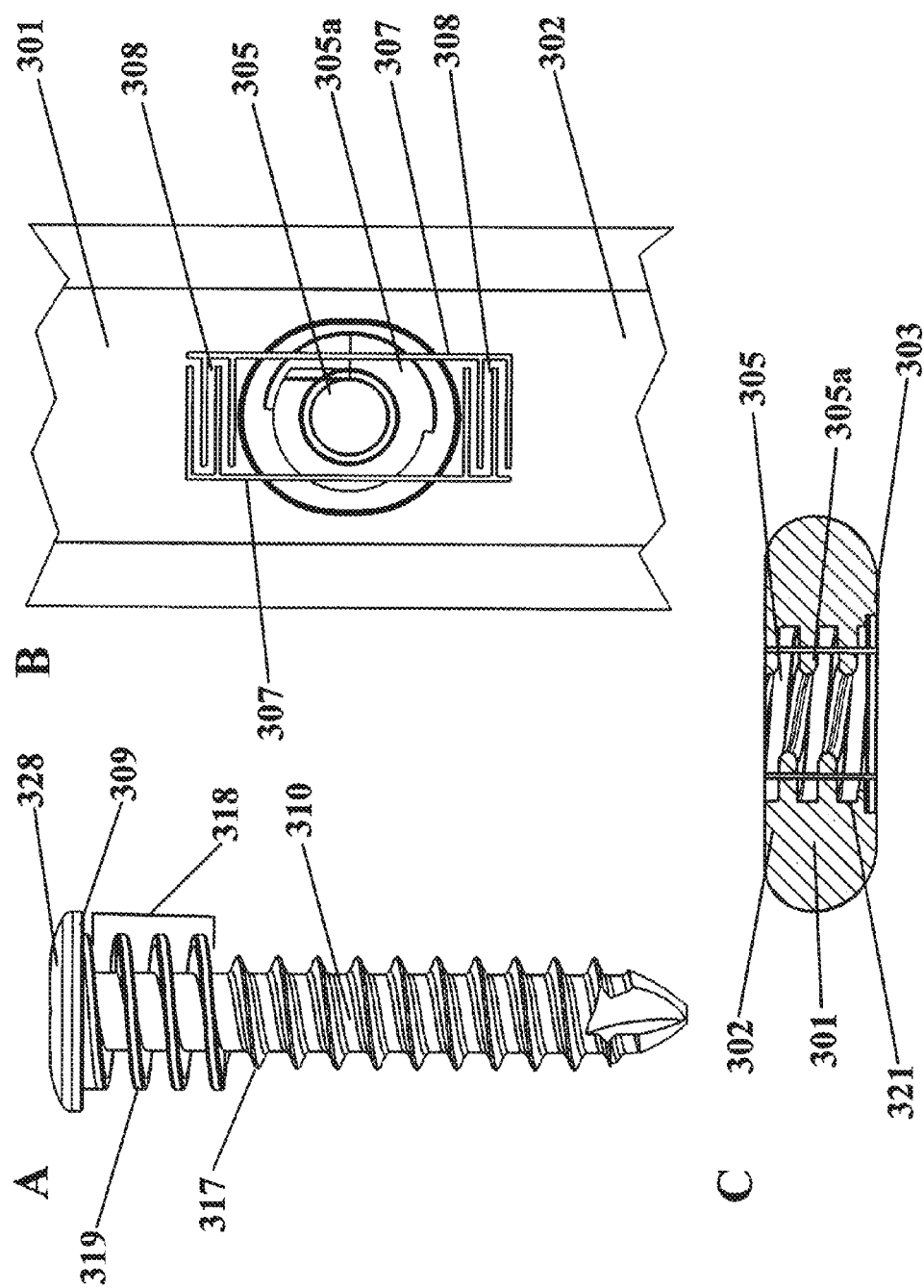
FIG. 3A illustrates a side view of an example of a screw with a thread that has a consistent core diameter, but an increased outer diameter in the vicinity of the screw head, in accordance with various embodiments.
FIG. 3B illustrates a top view of a bone plate having a corresponding thread in the plate hole that extends across the motion gap into the plate, in accordance with various embodiments.
FIG. 3C illustrates a transverse cross-sectional view of a bone plate having a corresponding thread in the plate hole that extends across the motion gap into the plate, in accordance with various embodiments.
Figure 4:
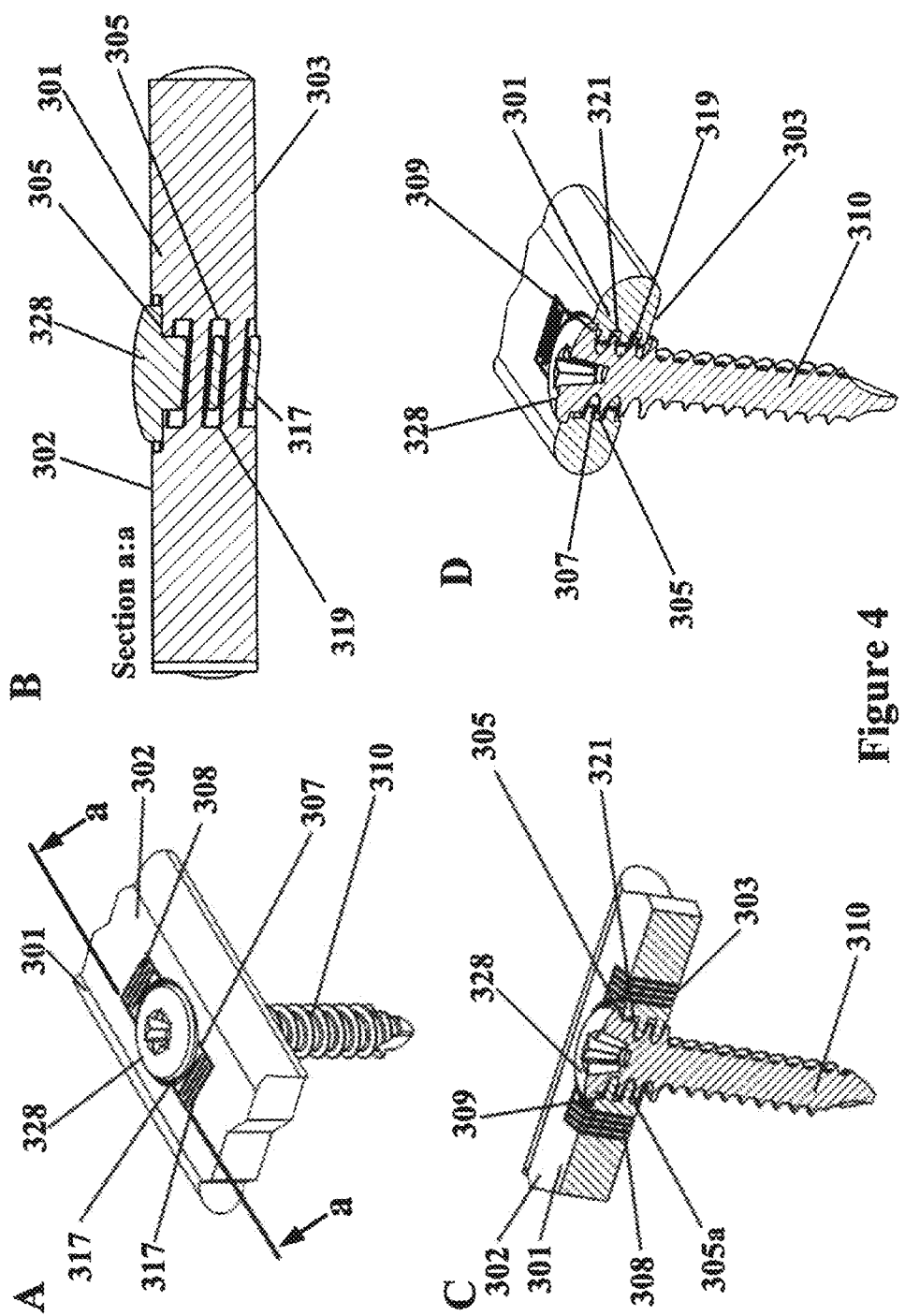
FIG. 4A illustrates a perspective assembly view of an embodiment of a bone plate assembly that limits deflection of the screw hole member out of the plane of the plate, while allowing for a controlled amount of translation of the screw hole member in the direction of the plate longitudinal axis, in accordance with various embodiments.
FIG. 4B illustrates a transverse cross-sectional view of the bone plate assembly illustrated in FIG. 4A, showing that the threaded feature of the screw head extends across the motion gap and into the plate to limit deflection of the screw hole member out of the plane of the plate, while allowing for a controlled amount of translation of the screw hole member in the direction of the plate longitudinal axis, in accordance with various embodiments.
FIG. 4C illustrates a partial longitudinal perspective view of the bone plate assembly illustrated in FIG. 4A, in accordance with various embodiments.
FIG. 4D illustrates a partial transverse perspective view of the bone plate assembly illustrated in FIG. 4A, in accordance with various embodiments.
Figure 5:
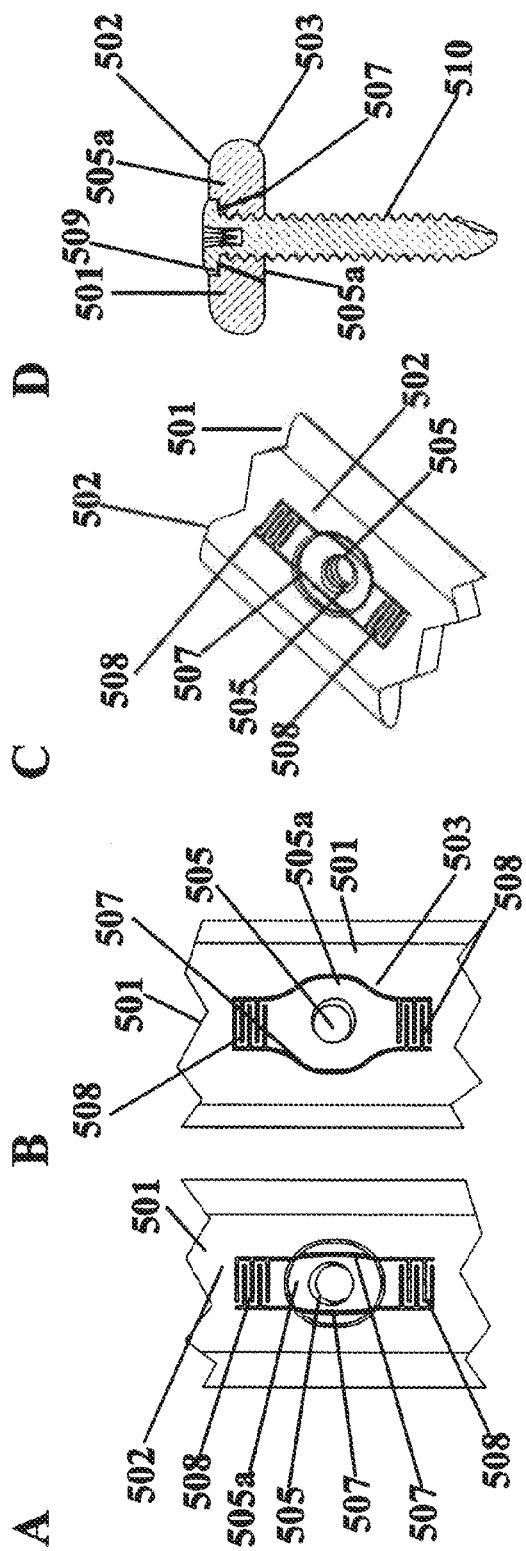
FIG. 5A illustrates a top view of an example of a bone plate in which the motion gaps adjacent to the screw hole diverge from the top surface to the lower surface of the plate, in accordance with various embodiments.
FIG. 5B illustrates a bottom view of the bone plate shown in FIG. 5A, in accordance with various embodiments.
FIG. 5C illustrates a perspective view of the bone plate shown in FIG. 5A, in accordance with various embodiments.
FIG. 5D illustrates a transverse cross-sectional view of the bone plate shown in FIG. 5A, in accordance with various embodiments.

FIGS. 3A, 3B, and 3C illustrate a side view, a top view, and a transverse cross-sectional view, respectively, of an example of a screw with a thread that has a consistent core diameter, but an increased outer diameter in vicinity of the screw head, and FIGS. 4A, 4B, 4C, and 4D illustrate a perspective assembly view, a transverse cross-sectional view, a partial longitudinal perspective view, and a partial transverse perspective view, respectively, of an embodiment of a bone plate assembly 301, showing that the threaded feature of the screw head extends across the motion gap and into the plate to limit deflection of the screw hole member out of the plane of the plate, while allowing for a controlled amount of translation of the screw hole member in the direction of the plate longitudinal axis, all in accordance with various embodiments.

As discussed above and as illustrated in FIGS. 3 and 4, a bone plate in accordance with the present disclosure may include elastic segments 308 that may be symmetrically arranged in proximity with the screw hole 305, for instance to enable translation of the screw hole member 305a in a principally axial direction. In some embodiments, screw hole member 305a may be guided to remain within the plane of the plate by a thread 321 that may extend from screw hole 305, across the motion gap 307, and into the plate member 301. In some embodiments, thread 321 may be characterized by an outer diameter that is considerably larger than the core diameter. For example, a suitable core diameter is in the range of 2 to 5 and a suitable outer diameter is in the range of 4 to 10.

In various embodiments, the locking screw 310 may include a correspondingly threaded head segment 318 with an outer diameter that is considerably larger than the core diameter. However, in various embodiments, the outer diameter of the thread 319 of the screw head segment 318 may be smaller than the outer diameter of thread 321 in screw hole member 305a. In various embodiments, the outer diameter of thread 319 in screw head segment 318 may remain large enough to extend across the motion gap 307 and into the plate member 301, once inserted into the screw hole 305. In some embodiments, screw head 328 may include a locking feature 309 at may enable rigid fixation of screw head 328 inside screw hole member 305a. In particular embodiments, once screw 310 is fixed to screw hole member 305a, screw hole member 305a may translate in a principally axial direction relative to the plate longitudinal axis, for instance, due to the difference in outer diameters between screw head 328, thread 319, and plate thread 321. However, in some embodiments, extension of screw head thread 319 across motion gap 307 and into plate member 301 may limit deflection of screw hole member 305a outside the plane of plate 301.

FIGS. 5A, 5B, 5C, and 5D illustrate a top view, a bottom view, a perspective view, and a transverse cross-sectional view, respectively, of an example of a bone plate 501 in which the motion gaps 507 adjacent to the screw hole 505 diverge from the top surface 502 to the lower surface 503 of plate 501, in accordance with various embodiments. In the illustrated example, elastic segments 508 may be symmetrically arranged in proximity with screw hole 505, for instance, to enable translation of the screw hole member 505a in a principally axial direction. In various embodiments, motion gaps 507 connecting symmetrically arranged elastic segments 508 may diverge from (angle away from) the upper plate surface 502 toward the lower plate surface 503. In various embodiments, these divergent motion gaps 507 may limit deflection of screw hole member 505a through upper surface 502 of the plate member 501. In some embodiments, the head diameter of the corresponding locking screw 510 may be sufficiently large to extend over motion gap 507 on upper surface 502 of plate member 501. For example, the head may extend over motion gap, when at rest, by about 0.1 mm-3 mm, for example, about 1 mm. In various embodiments, the locking feature 509 may thereby limit deflection of screw hole member 505a through bottom surface 503 of plate member 501.

Figure 6:
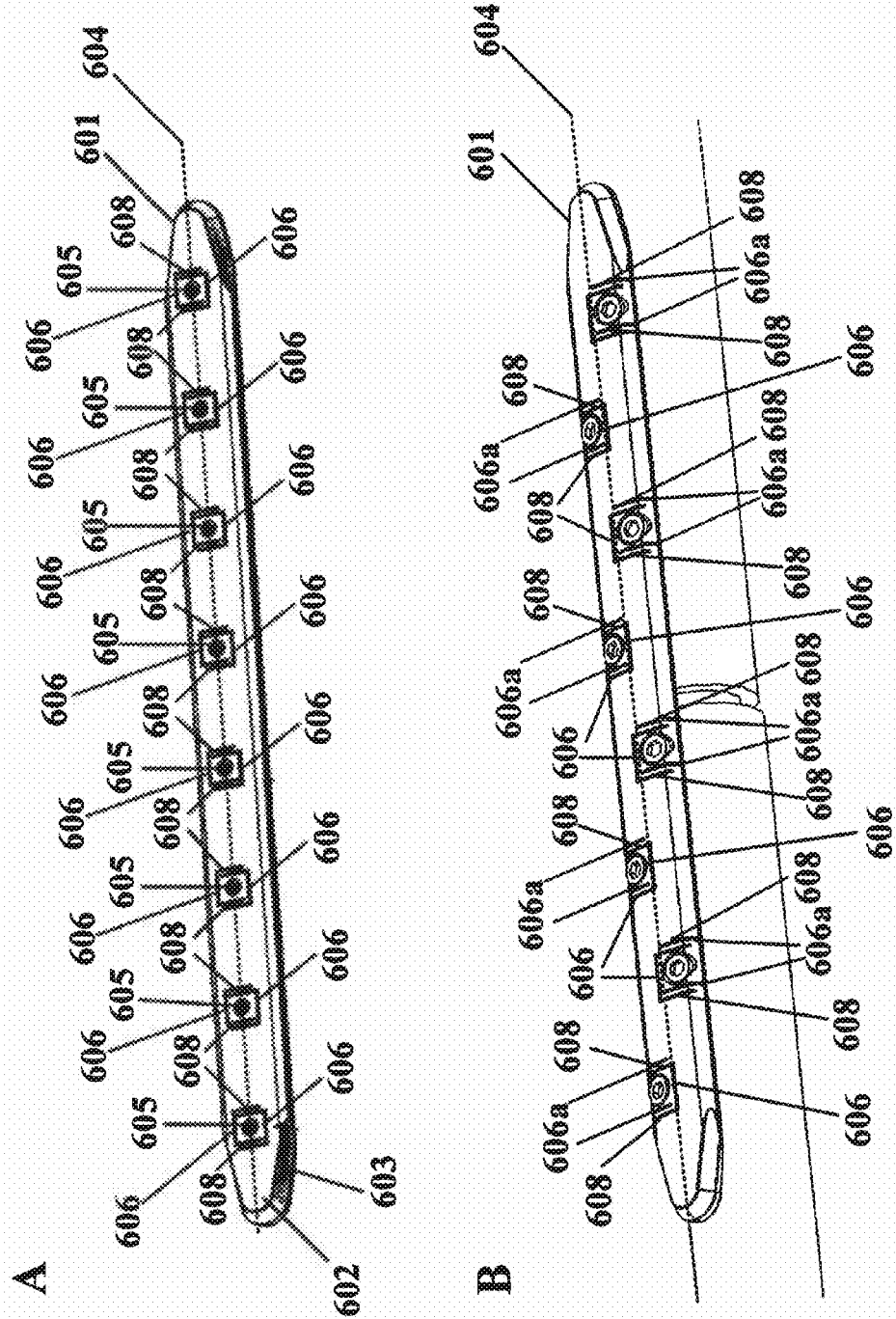
FIG. 6A illustrates a top view of another example of a bone plate for elastic fixation of a bone fracture, in accordance with various embodiments.
FIG. 6B illustrates a top view of another bone plate for elastic fixation of a bone fracture for use in combination with cylindrical bone segments, in accordance with various embodiments.

FIG. 6A illustrates a top view of another example of a bone plate for elastic fixation of a bone fracture, and FIG. 6B illustrates a top view of a further bone plate for elastic fixation of a bone fracture for use in combination with cylindrical bone segments, in accordance with various embodiments. In these embodiments, the bone plate 601 may have an upper surface 602 and a bone contacting surface 603, and it may define a longitudinal axis 604. In some embodiments, at least one receiving hole 605 for a fixation element may extend through the upper surface 602 and the bone contacting surface 603. In some embodiments, receiving hole 605 may be threaded for rigid engagement of a locking screw with a threaded head portion, or it may have a concave recess to accommodate a conventional compression screw. In some embodiments, receiving holes 605 may be disposed along the longitudinal axis 604 as shown in FIG. 6A. In other embodiments, receiving holes 605 may be spaced from the longitudinal axis 604, as shown in FIG. 6B.

Also included in some embodiments, in the vicinity of receiving hole 605 are one or more slots 606 extending from the upper surface 602 to the bone contacting surface 603. In various embodiments, at least one substantially C-shaped, E-shaped, or semi-circular slot 606 may extend around a substantial portion of receiving hole 605. In some embodiments, a corresponding slot 606a may extend from the opposite side of the periphery around receiving hole 605. In some embodiments, the end segments of slot 606 may overlap, but not intersect the end segments of corresponding slot 606a. Thus, in various embodiments, the overlapping slots 606 and 606a may enclose elastic beam elements (e.g., spring elements) 608 that may enable elastic translation of receiving hole 605 relative to bone plate 601 in a direction principally parallel to the longitudinal axis 604 of bone plate 601.

In the embodiment illustrated in FIG. 6B, elastic beam elements 608 may be formed by combining at least one substantially C-shaped, E-shaped or semi-circular slot 606 with one or more substantially linear slots 606a extending from the periphery of bone plate 601 in an essentially perpendicular manner to overlap but not intersect with the ends of slots 606.

Figure 7:
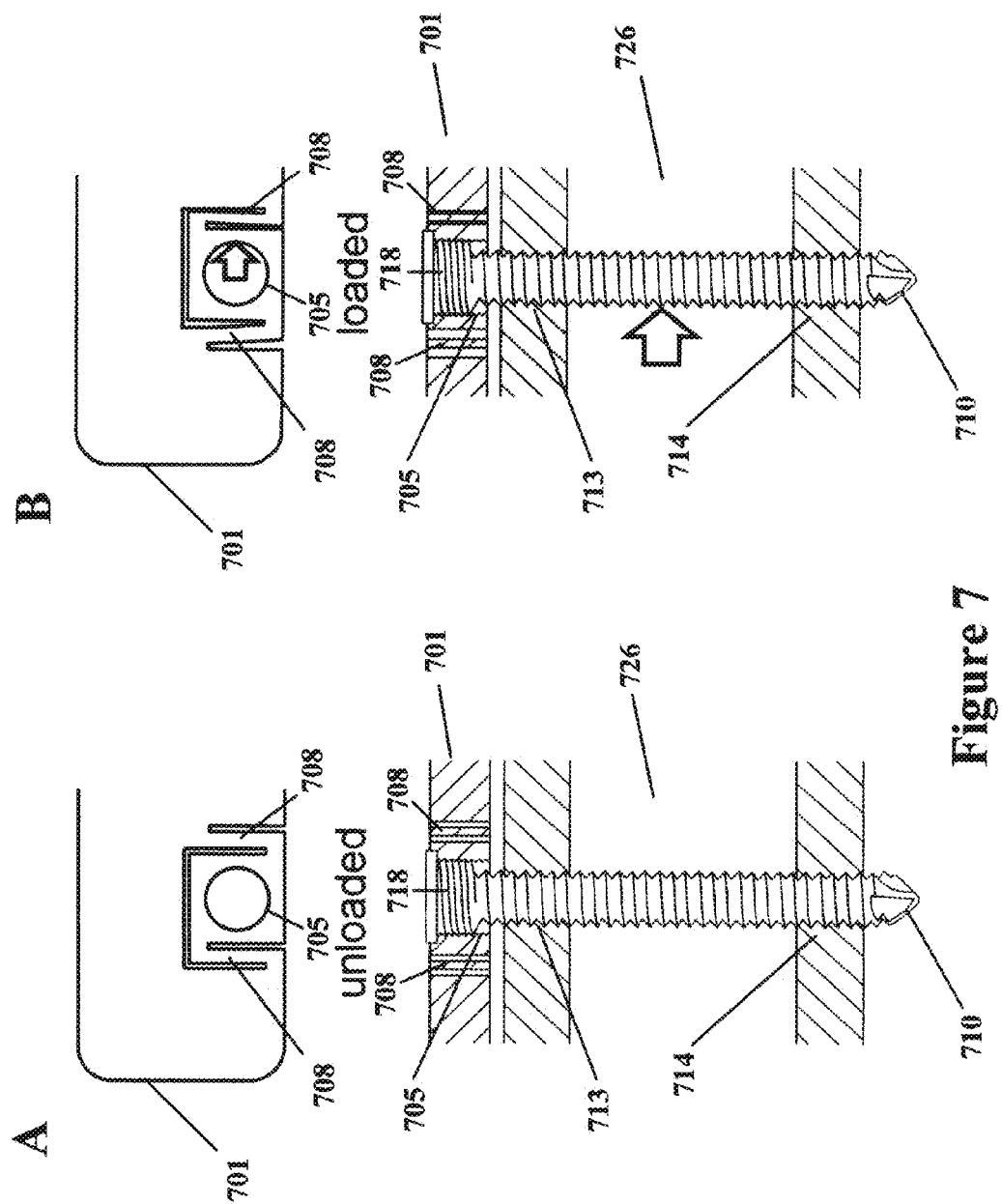
FIG. 7A illustrates a top view and a cross-sectional side view of an example of a bone plate for elastic fixation of a bone, shown in functional but unloaded association with a bone screw affixed to a cylindrical bone, in accordance with various embodiments.
FIG. 7B illustrates a top view and a cross-sectional side view of an example of a bone plate for elastic fixation of a bone, shown in functional loaded association with a bone screw affixed to a cylindrical bone, in accordance with various embodiments.

FIGS. 7A and 7B illustrate top and cross-sectional side views of an example of a bone plate 701 for elastic fixation of a bone, shown in functional but unloaded (FIG. 7A) association with a bone screw 710 affixed to a cylindrical bone 726, and shown in functional loaded (FIG. 7B) association with a bone screw 710 affixed to a cylindrical bone, in accordance with various embodiments. In the illustrated embodiment, a locking bone screw 710 is illustrated that may have a threaded head segment 718 for rigid engagement with receiving hole 705. In various embodiments, the screw 710 may be furthermore engaged in first cortex 713 and/or second cortex 714 of a substantially cylindrical bone 726. FIG. 7A illustrates an example of an unloaded construct, and FIG. 7B illustrates an example of how a load acting through bone 726 and onto locking screw 710 may induce translation of receiving hole 705 relative to the bone plate 701 by elastic deformation of elastic beam elements 708 between receiving hole 705 and bone plate 701.

Figure 8:
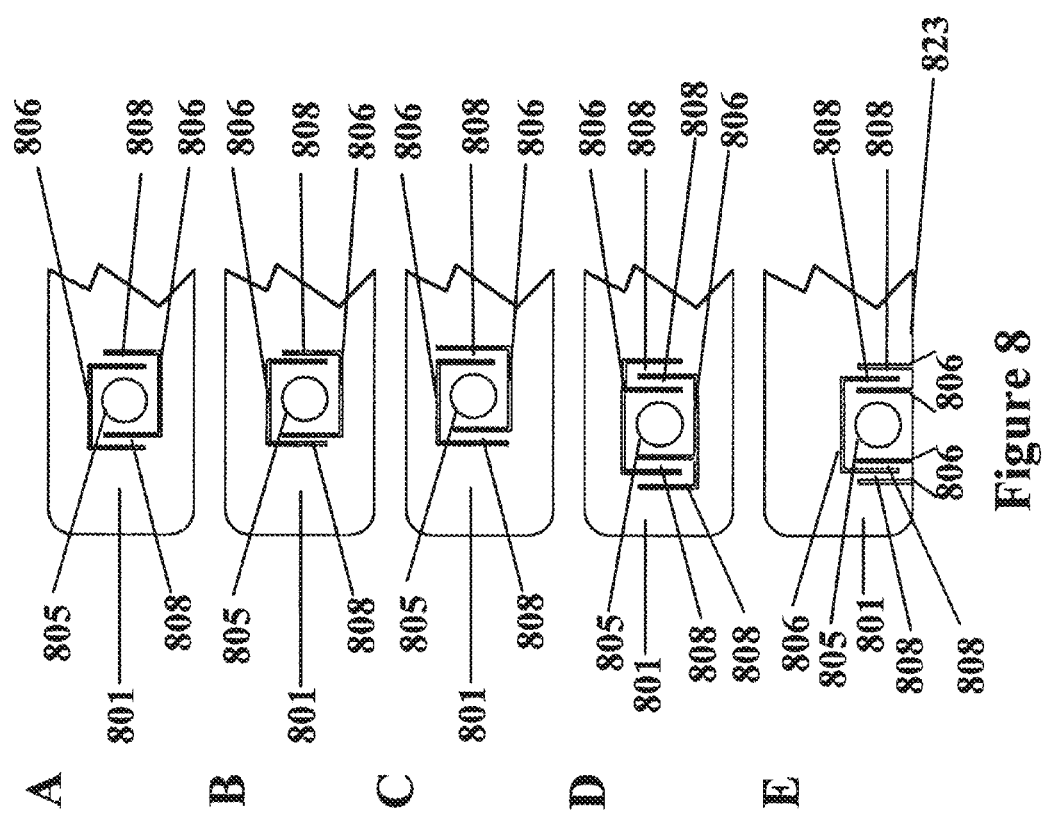
FIG. 8A illustrates a top view of an embodiment of a C-shaped flexible element, in accordance with various embodiments.
FIG. 8B illustrates a top view of another embodiment of a C-shaped flexible element wherein elastic beam elements are narrow to reduce stiffness, in accordance with various embodiments.
FIG. 8C illustrates a top view of another embodiment of a C-shaped flexible element wherein the elastic beam elements are elongated to reduce stiffness, in accordance with various embodiments.
FIG. 8D illustrates a top view of an E-shaped flexible element wherein elastic beam elements are narrow to reduce stiffness, in accordance with various embodiments.
FIG. 8E illustrates a top view of a flexible element that includes one E-shaped slot in combination with multiple linear slots, in accordance with various embodiments.

In various embodiments, the dimensions and/or the configuration of the spring elements (e.g., elastic beam elements) and/or slots may be varied in order to achieve a desired stiffness and range of elastic displacement of the bone plate relative to the receiving holes. FIG. 8A depicts an embodiment with thicker beam elements 808 as compared to beam elements 808 shown in FIG. 8B, the latter allowing for more flexible displacement of receiving hole 805 relative to bone plate member 801. Another example of a way to decrease the stiffness of the elastic elements is depicted in FIG. 8C, wherein the length of slot 806 is increased in order to increase the effective length of beam elements 808. Yet another example of a way to decrease the stiffness of the elastic element is depicted in FIG. 8D, wherein slots 806 are configured in a substantially E-shaped formation, which may yield an increased effective length of elastic beam elements 808. Another alternative embodiment of an elastic element is depicted in FIG. 8E, wherein receiving hole 805 is located in vicinity of plate edge 823. In this example, two slots 806 may overlap but not intersect each end of a C-shaped slot 806 to form elastic beam elements 808.

Figure 9:
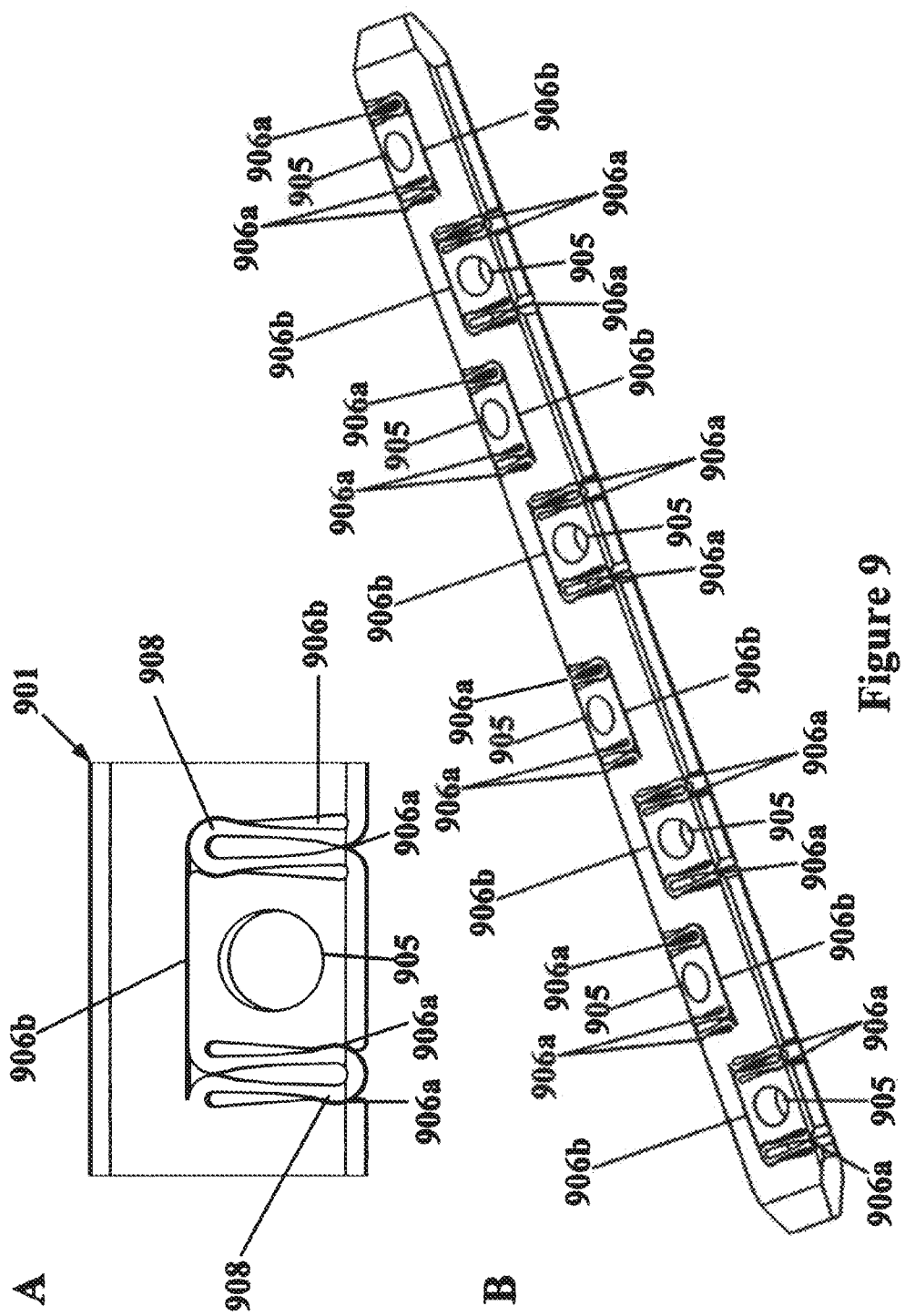
FIG. 9A illustrates a top view of a flexible element that includes a curvilinear E-shaped slot in combination with multiple linear slots, in accordance with various embodiments.
FIG. 9B illustrates a perspective view of a bone plate for elastic fixation of a bone fracture, incorporating the flexible elements shown in FIG. 9A, in accordance with various embodiments.

FIG. 9A illustrates a top view of a flexible element that includes a curvilinear E-shaped slot in combination with multiple linear slots 906, and FIG. 9B illustrates a perspective view of a bone plate 901 for elastic fixation of a bone fracture that incorporates the flexible elements 908 shown in FIG. 9A, in accordance with various embodiments. As illustrated in FIG. 9A, some embodiments of bone plates 901 may include one curvilinear E-shaped slot 906b in combination with multiple linear slots 906a, which together form elastic beam elements 908. In some embodiments, the curvilinear slots 906a may reduce peak stress and provide a more even strain distribution when loaded along the longitudinal axis of a bone plate 901. This embodiment is similar to that shown in FIG. 8D, in that the elastic beam elements 908 may be folded back on themselves. In some embodiments, each of the two folded elastic beams 908 associated with a receiving hole 905 may be oriented in opposite directions, wherein the folded end of one elastic beam element 908 may be oriented toward the edge of the bone plate 901, and the folded end of the other elastic beam element may be oriented toward the bone plate 901 midline. In various embodiments, the curvilinear fold of the elastic beam element 908 may fit closely within the E-shaped slot 906b, which arrangement may contribute to a stable association of receiving hole 905 with plate 901, while still allowing for controlled axial translation of receiving hole 905 relative to plate 901. FIG. 9B illustrates a perspective view of a bone plate having the curvilinear E-shaped slots 906b shown in FIG. 9k In this embodiment, the receiving holes 905 may be offset from the longitudinal axis, which may contribute to the stability and stiffness of bone plate 901.

Figure 10:
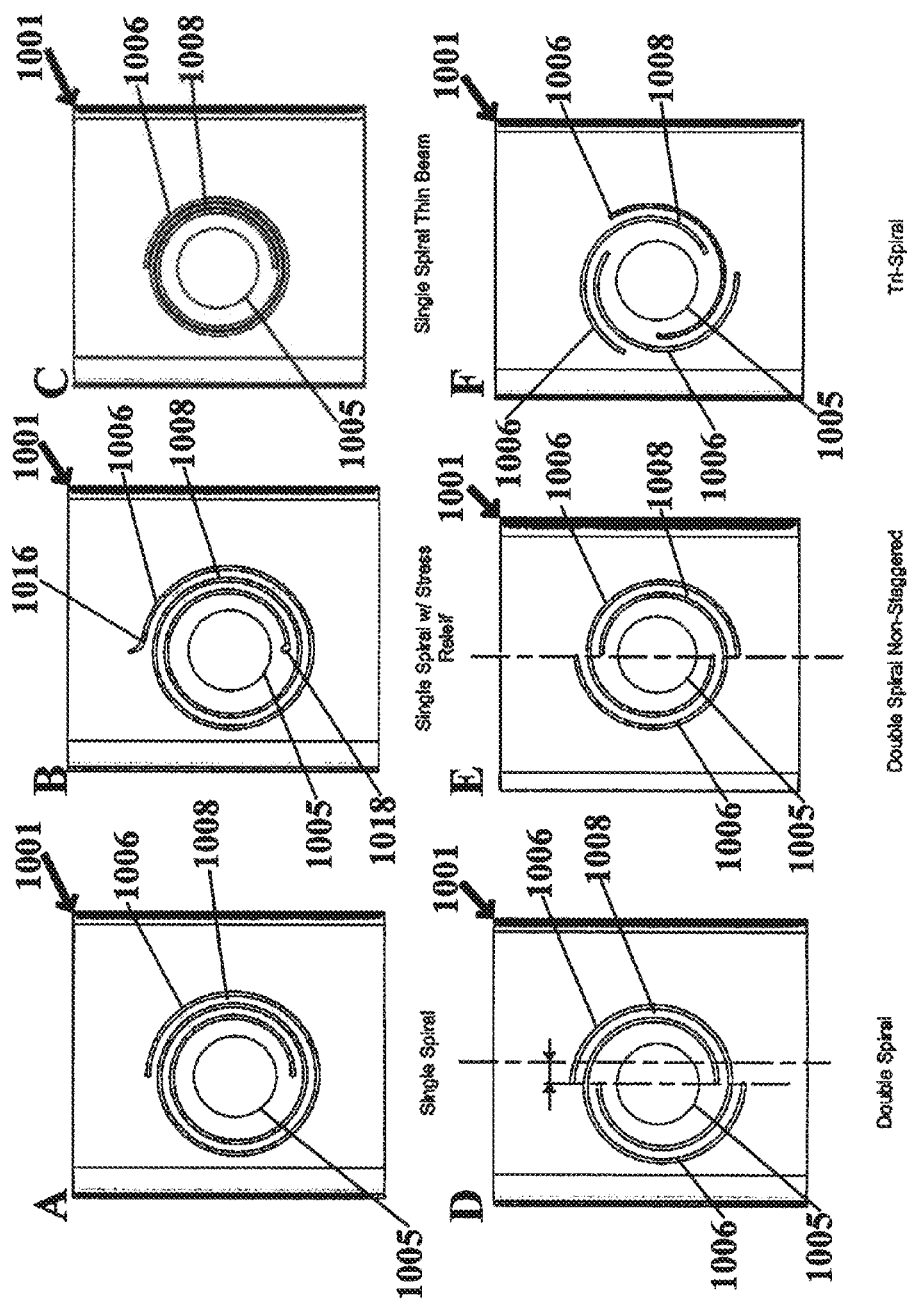
FIG. 10A illustrates a top view of a flexible element that includes a single spiral-shaped slot, in accordance with various embodiments.
FIG. 10B illustrates a top view of a flexible element that includes a single spiral-shaped slot with curvilinear and round elements on the outside and inside spiral ends, respectively, in accordance with various embodiments.
FIG. 10C illustrates a top view of a flexible element that includes a single spiral-shaped slot having a thin beam, in accordance with various embodiments.
FIG. 10D illustrates a top view of a flexible element that includes a pair of interlaced spiral-shaped slots, wherein the flexible element is offset from the midline of the bone plate, in accordance with various embodiments.
FIG. 10E illustrates a top view of a flexible element that includes a pair of interlaced spiral-shaped slots, wherein the flexible element is positioned at the midline of the bone plate, in accordance with various embodiments.
FIG. 10F illustrates a top view of a flexible element that includes three interlaced spiral-shaped slots, in accordance with various embodiments.

Some embodiments of the flexible fixation bone plates may include curvilinear and/or spiral-shaped slots. FIG. 10A illustrates a top view of a flexible element that includes of a single spiral-shaped slot 1006, FIG. 10B illustrates a top view of a flexible element that includes a single spiral-shaped slot 1006 with curvilinear 1016 and round elements 1018 on the outside and inside spiral ends, respectively, FIG. 10C illustrates a top view of a flexible element that includes a single spiral-shaped slot 1006 having a thin elastic beam element 1008, FIG. 10D illustrates a top view of a flexible element that includes a pair of interlaced spiral-shaped slots 1006, wherein the flexible element is offset from the midline of the bone plate 1001, FIG. 10E illustrates a top view of a flexible element that includes a pair of interlaced spiral-shaped slots 1006, wherein the flexible element is positioned at the midline of the bone plate 1001, and FIG. 10F illustrates a top view of a flexible element that includes three interlaced spiral-shaped slots 1006, all in accordance with various embodiments.

FIG. 10A depicts another embodiment of an elastic element. In this embodiment, a single spiral-shaped slot 1006 may be positioned around receiving hole 1005. In various embodiments, the spiral slot 1006 may circumscribe receiving hole 1005 once or multiple times, creating elastic beam element 1008 where it overlaps. In various embodiments, in order to reduce stress concentrations at the spiral ends, circular 1018 or curvilinear 1016 elements may be added to the ends of slot 1006 as shown in FIG. 10B, or the beam elements 1008 may be tapered. As with the embodiments shown in FIG. 8A and 8B, in various embodiments, beam elements 1008 may be configured to be thinner, as shown in FIG. 10C, allowing for more flexible displacement of receiving hole 1005 relative to bone plate member 1001. In various embodiments, increasing the length of spiral beam element 1008 also may allow for increased flexibility.

As shown in FIGS. 10D and 10E, receiving holes 1005 may be located along the midline of plate 1001, or at a distance from the longitudinal axis of plate 1001. For example, in various embodiments, if receiving holes 1006 are arranged in an alternating staggered pattern relative to the longitudinal midline of plate 1001, they may provide multi-planar fixation to improve the strength of the fixation between plate 1001 and the underlying bone. Both FIGS. 10D and 10E illustrate spiral slots 1006 that include two interlaced spirals. One of skill in the art will appreciate that additional spiral slots 1006 may be used, such as the three-slot 1006 arrangement depicted in FIG. 10F.

Figure 11:
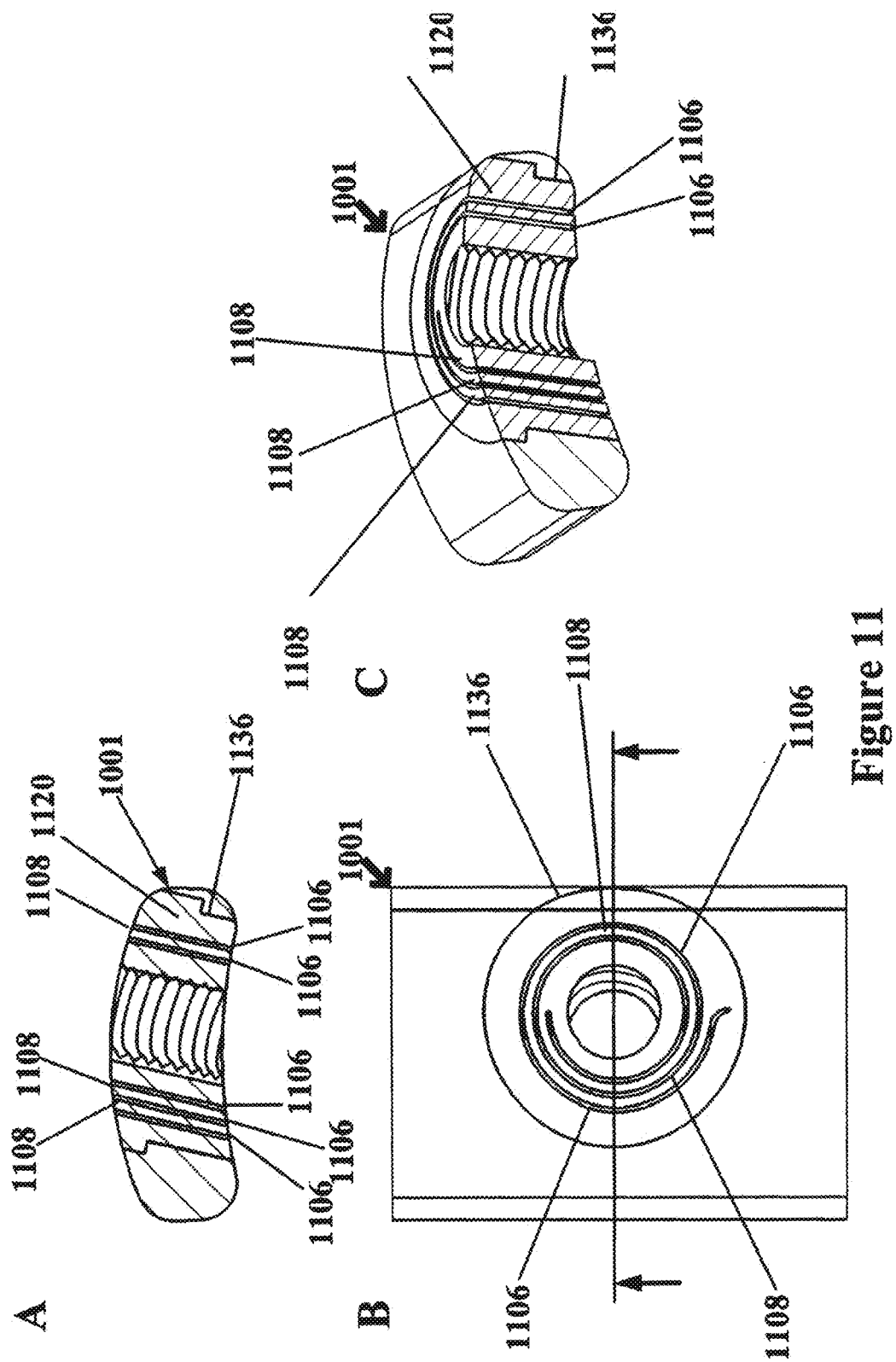
FIG. 11A illustrates a side view of a bone plate wherein the flexible element is a separate, removable element that is configured to be inserted into an enlarged receiving hole, in accordance with various embodiments.
FIG. 11B illustrates a top view of the flexible element of FIG. 11A, in accordance with various embodiments.
FIG. 11C illustrates a perspective view of the flexible element of FIG. 11A wherein the flexible element is a separate, removable element that is configured to be inserted into an enlarged receiving hole, in accordance with various embodiments.

FIGS. 11A, 11B, and 11C illustrate three views of another embodiment of a flexible element. In this embodiment of bone plate 1101, slot 1106 and elastic beam element 1108 may be located on a separate, removable plug element 1120 that may be adapted to be inserted into an enlarged receiving hole 1136. In an alternate embodiment, removable plug element 1120 may be an integral component of an enlarged head of a bone screw that engages the correspondingly enlarged receiving hole 1136.

Figure 12:
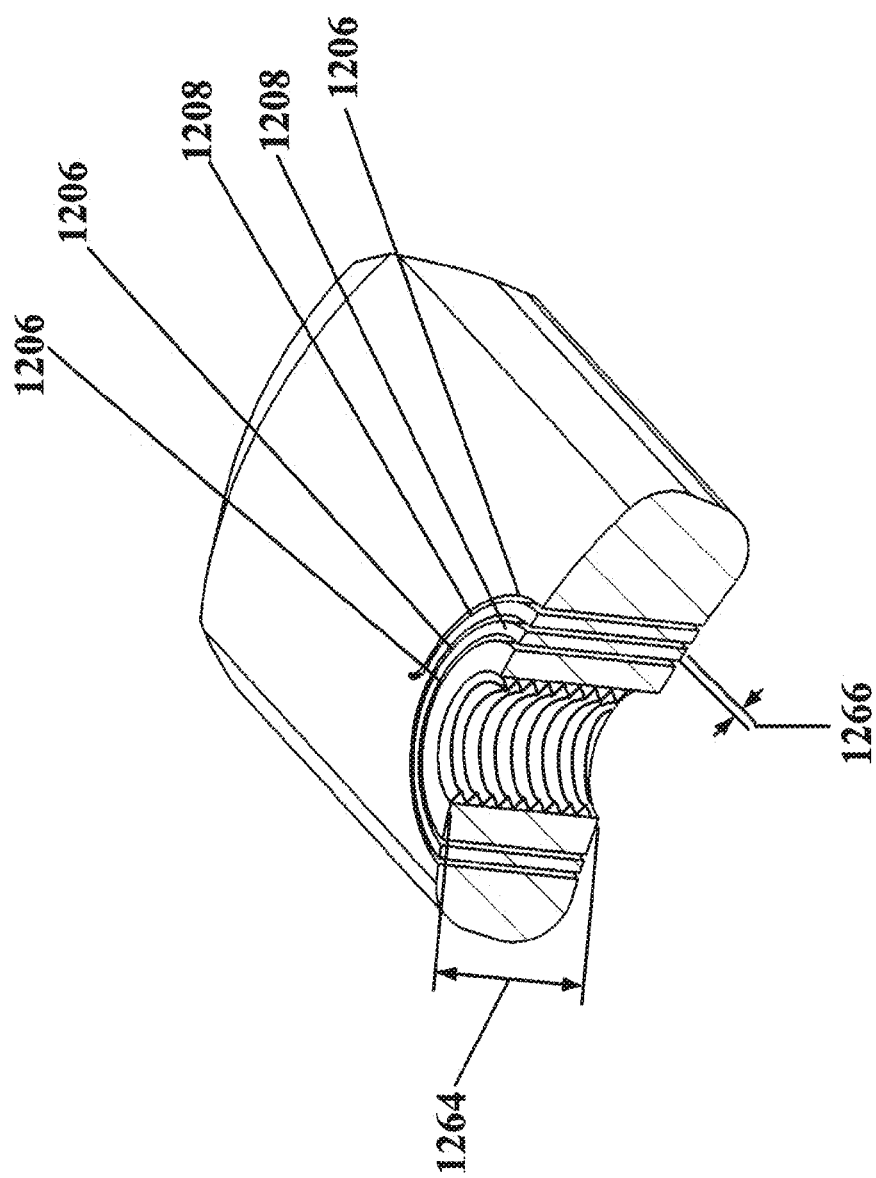
FIG. 12 illustrates a cross-sectional perspective view of a flexible element, showing the ratio of beam width to plate height, in accordance with various embodiments.

FIG. 12 depicts a cross-sectional perspective view of another embodiment, showing the dimensions of beam element 1208 and slot 1206. Generally, beam elements 1208 may be considerably higher (thicker) than they are wide. For instance, in some embodiments, the ratio of the beam height 1264 to the beam width 1266 may vary from about 2 (2 to 1) to about 12 (12 to 1), for instance from about 6 (6 to 1) to about 9 (9 to 1). In various embodiments, receiving holes 1205 associated with flexible elements as described herein may or may not have features for positive locking of a bone screw or fastener. For instance, in embodiments lacking positive locking mechanisms, the flexible spring element may act to relieve stress at the plate-bone interface. In embodiments having positive locking mechanisms, the flexible element may provide flexible plate fixation to allow small relative motion between the plate and the bone, which in turn may induce interfragmentary motion and promote bone healing.

Figure 13A:
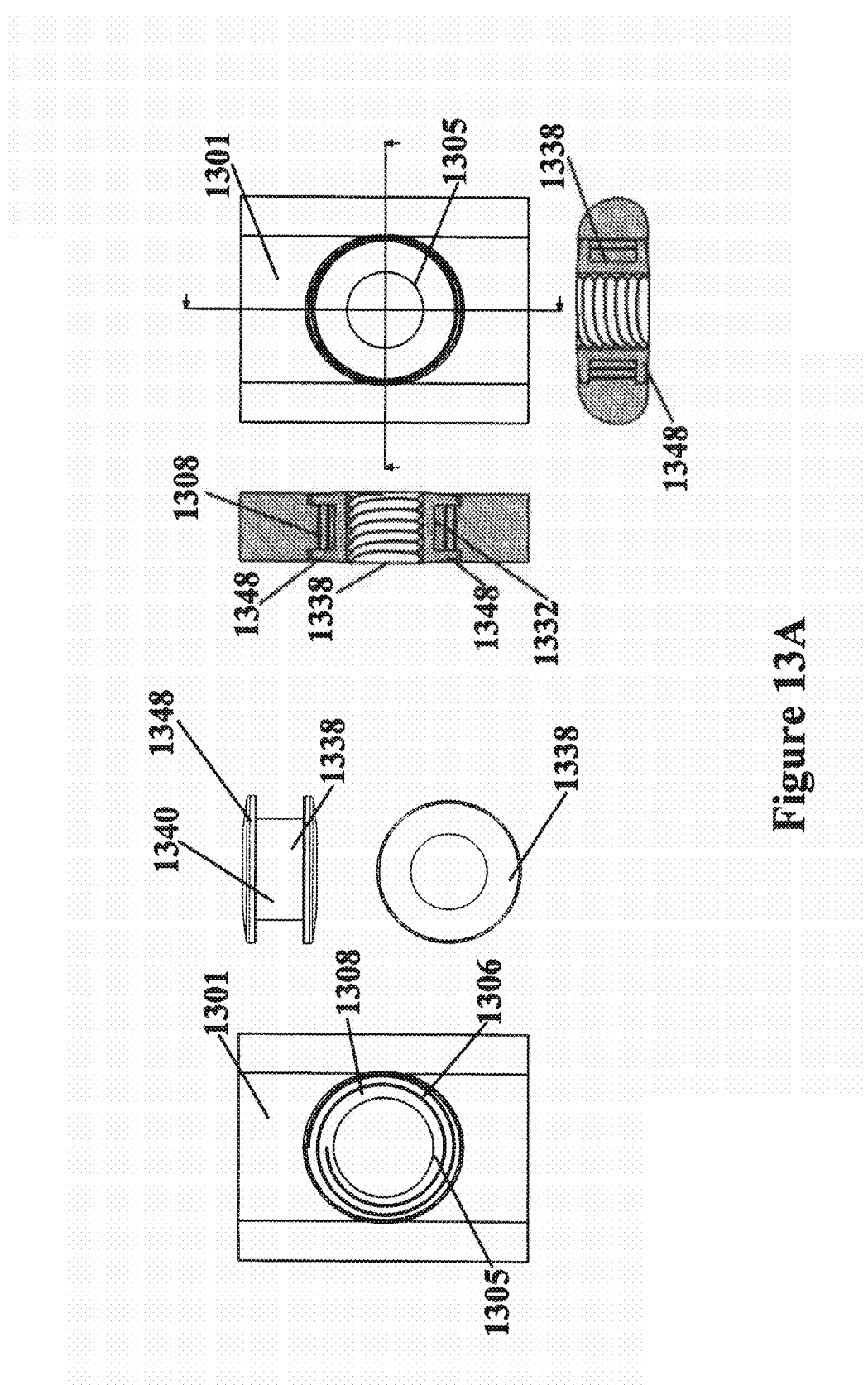
FIG. 13A illustrates several views of a flexible element coupled with a rivet configured to protect the flexible element from excessive deformation perpendicular to the plane of the plate, in accordance with various embodiments.
Figure 13B:
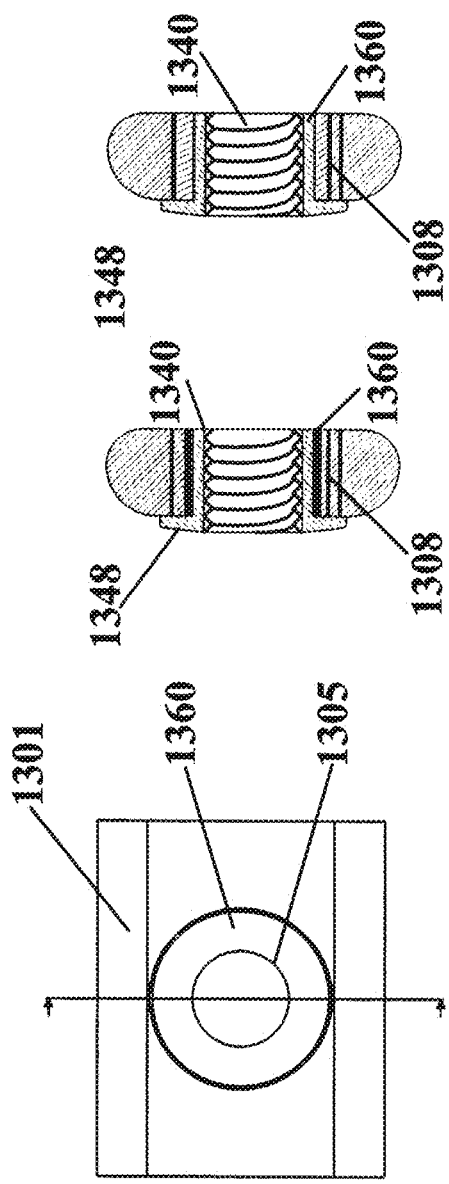
FIG. 13B illustrates several views of a flexible element coupled with a half-rivet configured to protect the flexible element from excessive deformation perpendicular to the plane of the plate, in accordance with various embodiments.
Figure 13C:
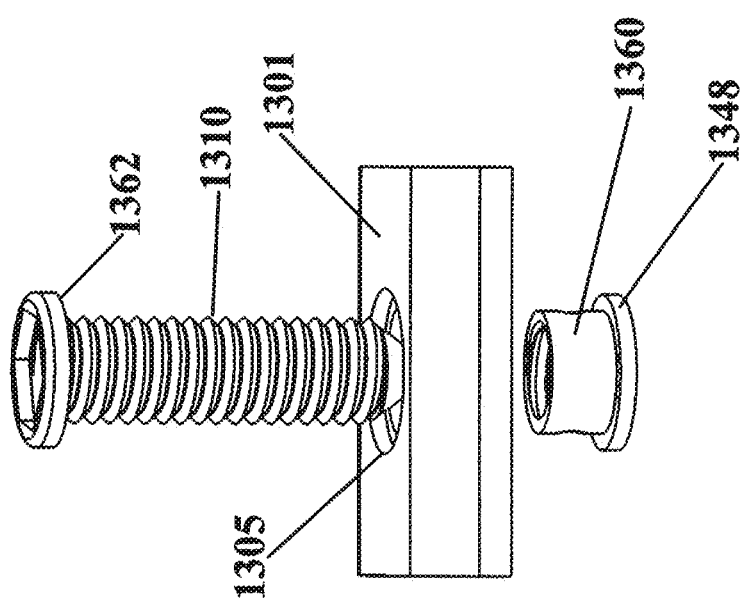
FIG. 13C illustrates a perspective view of a half rivet configured to protect the flexible element from excessive deformation perpendicular to the plane of the plate, wherein the half-rivet is coupled with a customized bone screw, in accordance with various embodiments.

In further embodiments, FIG. 13A illustrates several views of a flexible element 1308 used in conjunction with a rivet 1340 configured to protect the flexible element 1308 from excessive deformation perpendicular to the plane of the plate 1301, FIG. 13B illustrates several views of a flexible element 1308 used in conjunction with a half-rivet 1360 configured to protect the flexible element 1308 from excessive deformation perpendicular to the plane of the plate 1301, and FIG. 13C illustrates a perspective view of a half rivet 1360 configured to protect the flexible element 1308 from excessive deformation perpendicular to the plane of the plate 1301, wherein the half-rivet 1360 is used together with a customized bone screw 1310, all in accordance with various embodiments.

As illustrated in FIG. 13A, the elastic element 1308 may include a spiral-shaped slot 1306 positioned around receiving hole 1305, and the spiral slot 1306 may circumscribe receiving hole 1305 once or multiple times, creating elastic beam element 1308 where it overlaps. In this embodiment, a rivet 1338 may be provided in receiving hole 1305, and may be configured to protect elastic beam element 1308 from excessive deformation perpendicular to the plane of plate 1301. In various embodiments, rivet 1338 may have a shoulder 1348 on each side of a central cylinder 1340 to restrict flexion of elastic beam element 1308 that may occur within the plane of plate 1301. In embodiments, the inner diameter of the central cylinder 1340 of rivet 1338 may be threaded for rigid locking with the threaded head of a bone screw 1310. Depending on plate 1301 thickness, the rivet shoulders 1348 may rest on the surface of the plate 1301, or may be recessed into the plate 1301. In various embodiments wherein shoulder 1348 is recessed, the longitudinal dimension of the recess may be larger than the corresponding dimension of rivet shoulder 1348 to allow rivet translation along the plate 1301 longitudinal axis, while constraining rivet 1338 translation in a transverse direction.

In various embodiments, for assembly, rivet 1338 may include two parts that may be inserted from opposite sides into receiving hole 1305, and the two parts may be rigidly coupled to each other, for instance by laser welding or by a thread feature between central cylinder 1340 and shoulder 1348. Alternatively, as illustrated in FIG. 13B, rivet 1338 may have only one shoulder 1348 to form a "half-rivet" 1360, which may limit deformation of elastic beam element 1308 in only one direction. In various embodiments, half-rivet 1360 may include an externally threaded central cylinder 1340 for rigid engagement to elastic beam element 1308. Alternatively, in some embodiments, half-rivet 1360 may be attached to elastic beam element 1308 using a press fit between central cylinder 1340 and elastic beam element 1308. In embodiments, half-rivet 1360 may be used in combination with a customized bone screw 1310 as shown in FIG. 13C, which may include a head that incorporates a corresponding shoulder element 1362. Thus, in various embodiments, upon screw insertion, elastic beam element 1308 may be confined between shoulder 1348 of half-rivet 1360 and the corresponding shoulder 1362 of the screw head, with the remainder of the screw head resting inside central cylinder 1340 of half-rivet 1360.

Figure 14:
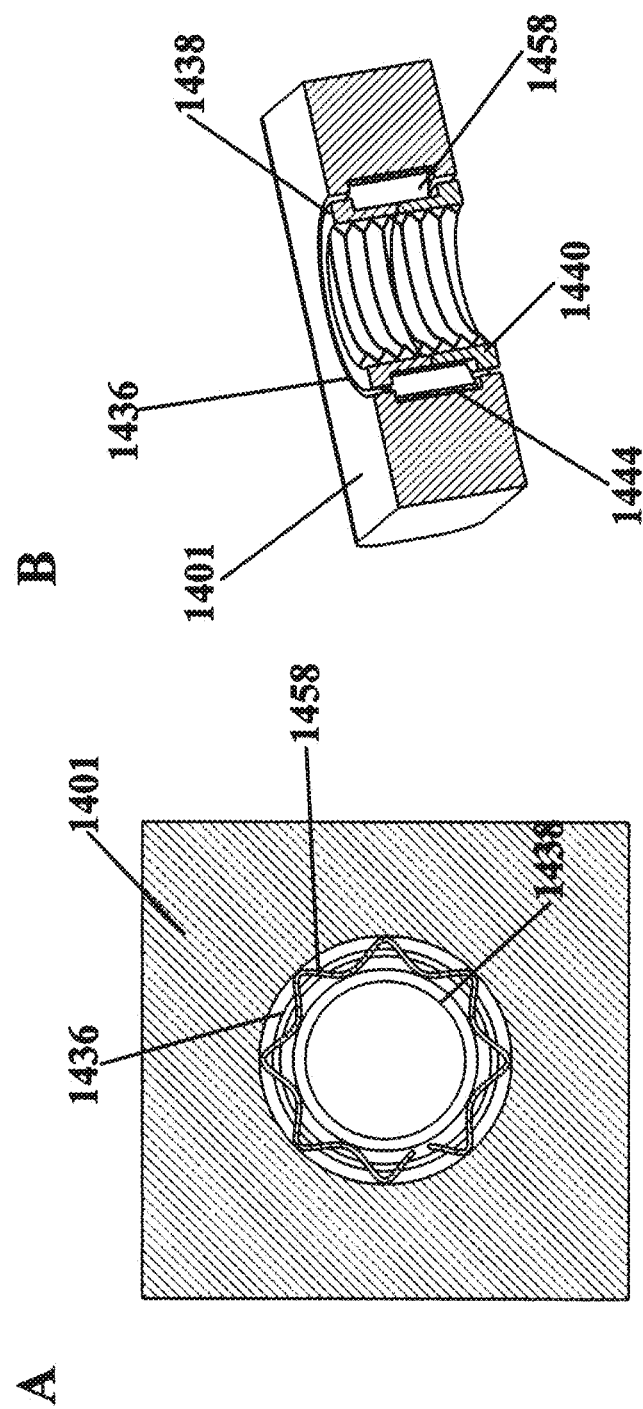
FIG. 14A illustrates a cross-sectional view of a rivet elastically suspended inside a receiving hole in a bone plate using a discrete spring element, in accordance with various embodiments.
FIG. 14B illustrates a perspective view of a rivet elastically suspended inside a receiving hole in a bone plate using a discrete spring element, in accordance with various embodiments.
Figure 15:
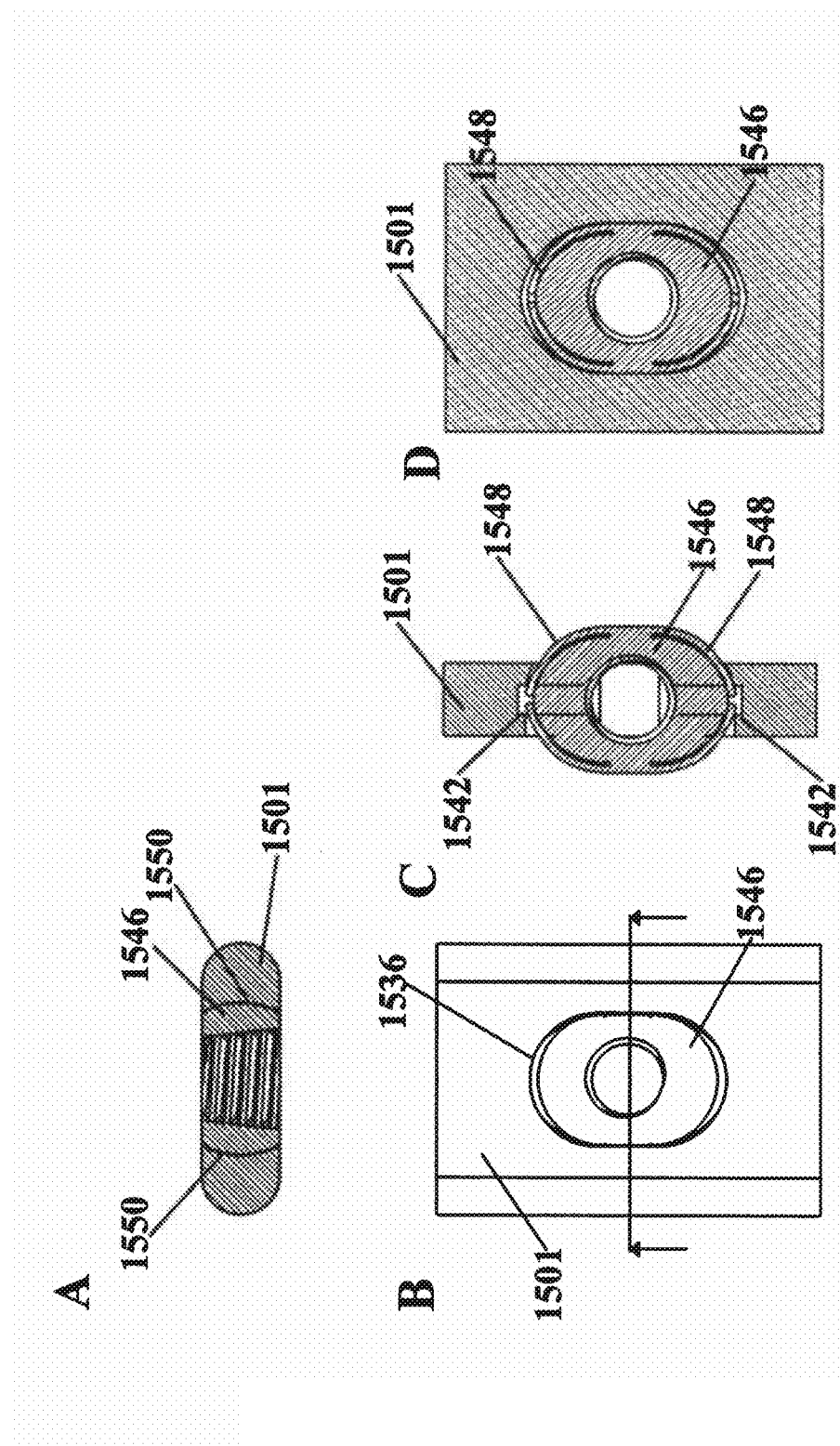
FIG. 15A illustrates a transverse cross-sectional view of a threaded insert that is suspended with spring elements in a central position within a receiving hole, whereby the spring elements are rigidly coupled to or part of a threaded insert, in accordance with various embodiments.
FIG. 15B illustrates a top view of the device shown in FIG. 15A, in accordance with various embodiments.
FIG. 15C illustrates a partial cutaway view of the device shown in FIG. 15A, showing placement of an insert, in accordance with various embodiments.
FIG. 15D illustrates a planar cross-sectional view of the device shown in FIG. 15A, in accordance with various embodiments.

In various other embodiments shown in FIGS. 14A and 14B, rivet 1438 may be elastically suspended inside receiving hole 1436 using a discrete spring element 1458. In some embodiments, spring element 1458 may include a corrugated metal strip 1444, that may circumscribe central cylinder 1440 of rivet 1438, and that may center rivet 1438 inside receiving hole 1436, while allowing for elastic translation of rivet 1438 within the plane of plate 1401. In some embodiments, spring element 1458 may further retain rivet 1438 inside the plane of plate 1401. The inner diameter of central cylinder 1440 of rivet 1438 may be threaded in some embodiments for rigid locking with the threaded head of a bone screw.

FIGS. 15A, 15B, 15C, and 15D illustrate a cross-sectional view, a top view, a partial cutaway view showing placement of an insert 1546, and a planar cross-sectional view, respectively, of another embodiment, in which a threaded insert 1546, once inserted into insert receiving hole 1536, may translate along the longitudinal plate axis within the plane of plate 1501. In various embodiments, threaded insert 1546 may be suspended with spring elements (e.g., flexible elements) 1548 in a central position within insert receiving hole 1536, whereby spring elements (e.g., flexible elements) 1548 may be rigidly coupled to or part of threaded insert 1546. In some embodiments, opposite sides of threaded insert 1546 may have a convex cylindrical surface 1550 adapted to securely retain threaded insert 1546 within the plane of plate 1501. In various embodiments, for installation, threaded insert 1546 may be first rotated perpendicular to the plate surface, then inserted into insert receiving hole 1536, and finally rotated by 90 degrees so that its upper surface is parallel to the upper surface of plate 1501. In some embodiments, spring elements (e.g., flexible elements) 1548 may engage with (e.g., snap into) a corresponding recess 1542 in plate 1501 to ensure that upon insertion, threaded insert 1546 remains rotationally secured within the plane of plate 1501.

Figure 16:
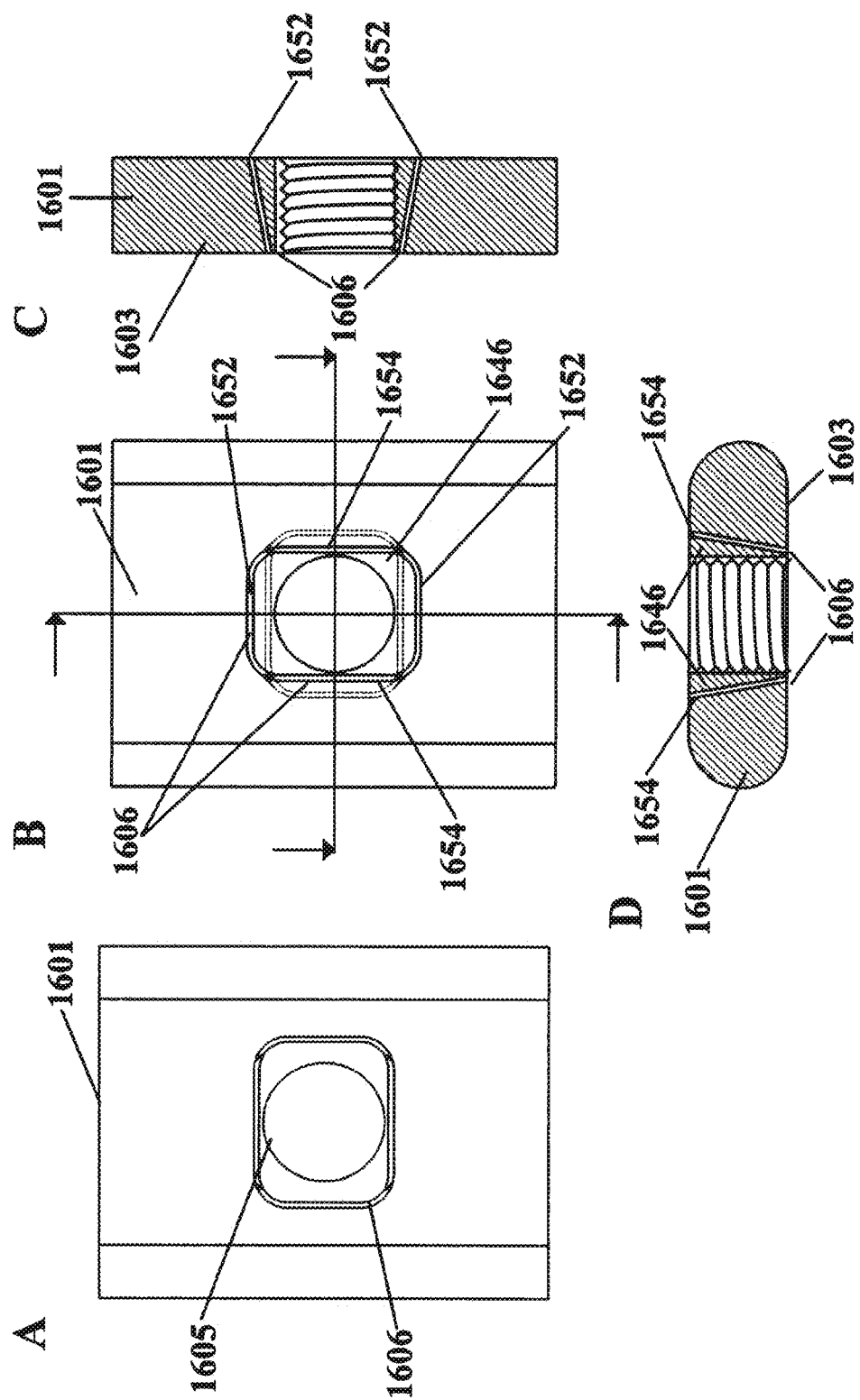
FIG. 16A illustrates a top view of a threaded insert that is generated from the bone plate by introducing a slot that circumscribes the receiving hole, in accordance with various embodiments.
FIG. 16B illustrates a schematic view of the device shown in FIG. 16A, in accordance with various embodiments.
FIG. 16C illustrates a longitudinal cross-sectional view of the device shown in FIG. 16A, in accordance with various embodiments.
FIG. 16D illustrates a transverse cross-sectional view of the device shown in FIG. 16A, in accordance with various embodiments.

In further embodiments, FIG. 16A illustrates a top view of a threaded insert 1646 that is generated from the bone plate 1601 by introducing a slot 1606 that circumscribes the receiving hole 1605, FIG. 16B illustrates a schematic view of the device shown in FIG. 16A, FIG. 16C illustrates a longitudinal cross-sectional view of the device shown in FIG. 16A, and FIG. 16D illustrates a transverse cross-sectional view of the device shown in FIG. 16A, all in accordance with various embodiments. As illustrated in various embodiments, a threaded insert 1646 may be generated from plate 1601 by introducing a slot 1606 that circumscribes receiving hole 1605. In various embodiments, slot 1606 may be introduced in an anti-parallel manner, whereby two opposing sections 1652 of slot 1606 converge toward the lower side 1603 of plate 1601, while two other opposing sections 1654 diverge toward the lower side 1603 of plate 1601. Hence, in these embodiments, the anti-parallel slot 1606 may enable threaded insert 1646 to translate relative to plate 1601 within the confines of the slot width, and without being able to disassociate from plate 1601.

Figure 17:
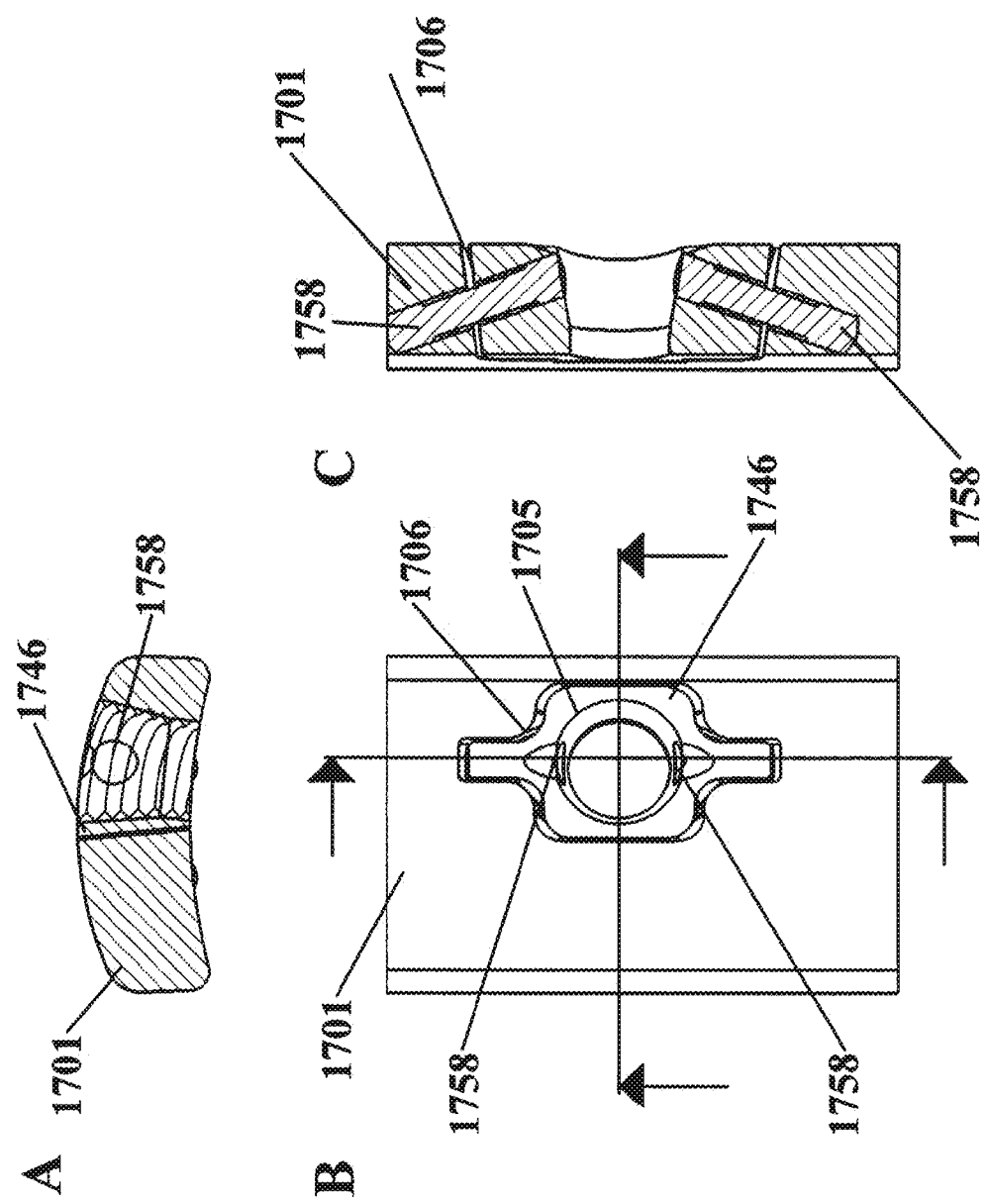
FIG. 17A illustrates a transverse cross-sectional view of a threaded insert formed by the introduction of a slot that circumscribes the receiving hole in an antiparallel manner and suspended (centered) inside a bone plate using flexible elements, in accordance with various embodiments.
FIG. 17B illustrates a top view of the device illustrated in FIG. 17A, in accordance with various embodiments.
FIG. 17C illustrates a longitudinal cross-sectional view of the device illustrated in FIG. 17A, in accordance with various embodiments.

In still other embodiments, FIG. 17A illustrates a transverse cross-sectional view of a threaded insert 1746 formed by the introduction of a slot 1706 that circumscribes the receiving hole 1705 in an anti-parallel manner and suspended (centered) inside a bone plate 1701 using flexible elements 1758, FIG. 17B illustrates a top view of the device illustrated in FIG. 17A, and FIG. 17C illustrates a longitudinal cross-sectional view of the device illustrated in FIG. 17A, all in accordance with various embodiments. As illustrated in FIGS. 17A-C, threaded insert 1746 may be formed by the introduction of a slot 1706 that circumscribes receiving hole 1705 in an antiparallel manner as described above, and threaded insert 1746 may be suspended (centered) inside plate 1701 using flexible elements 1758. In an exemplary embodiment, these flexible elements 1758 may be cylindrical in shape and comprised of a polymer, and may provide a flexible connection between threaded insert 1746 and plate 1701, while the anti-parallel slot ensures that threaded insert 1746 remains securely captured in plate 1701.

Figure 18:
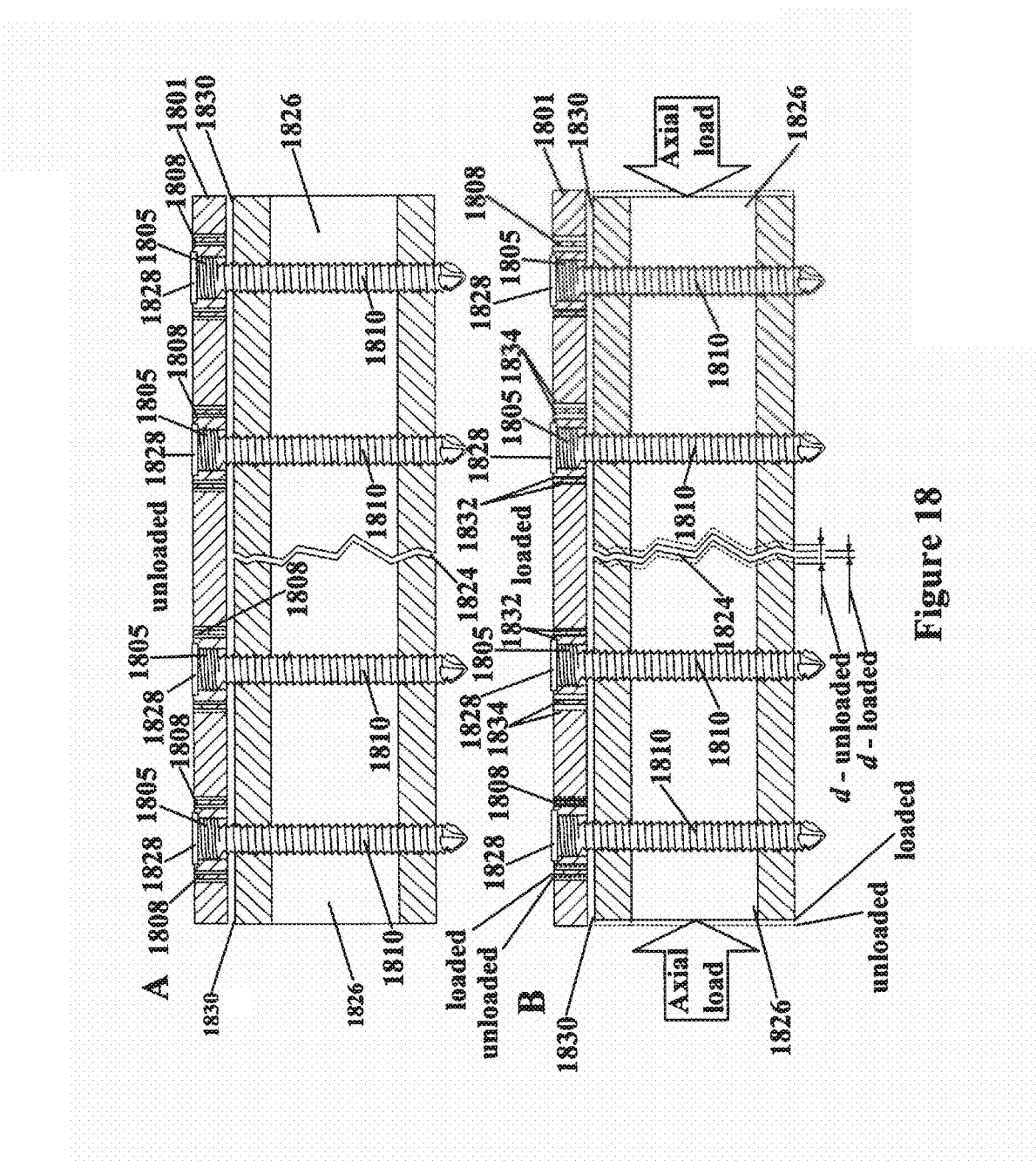
FIG. 18A illustrates a cross-sectional side view of a bone plate for elastic fixation of a bone fracture, shown in functional but unloaded association with locking bone screws for spanning a bone fracture in a cylindrical bone, in accordance with various embodiments.
FIG. 18B illustrates a cross-sectional side view of a bone plate for elastic fixation of a bone fracture, shown in functional association with locking bone screws for spanning a bone fracture in a cylindrical bone, wherein axial compression of the cylindrical bone segments induces parallel motion at the fracture, in accordance with various embodiments.

In other embodiments, FIG. 18A illustrates a cross-sectional side view of a bone plate for elastic fixation of a bone fracture, shown in functional but unloaded association with locking bone screws for spanning a bone fracture in a cylindrical bone, and FIG. 18B illustrates a cross-sectional side view of a bone plate for elastic fixation of a bone fracture, shown in functional association with locking bone screws for spanning a bone fracture in a cylindrical bone, wherein axial compression of the cylindrical bone segments induces parallel motion at the fracture, both in accordance with various embodiments.

Thus, in order to illustrate a method for elastic fixation of a bone fracture, FIG. 18A depicts a cross-sectional view of an embodiment for elastic fixation of a bone fracture 1824 with a bone plate 1801 that may be attached to two bone segments 1826. In this configuration, each bone segment 1826 may be connected by one or more locking bone screws 1810 to receiving holes 1805 that may be connected with elastic elements 1808 to bone plate 1801. In embodiments, the screw heads 1828 of bone screws 1810 may be rigidly connected to receiving holes 1805, for instance by matching thread features on screw heads 1828 with those on the receiving holes 1805. In embodiments, this locking mechanism between screw heads 1828 and receiving holes 1805 may enable bone plate 1801 to remain elevated above bone surface 1830, while providing elastic fixation between bone segments 1826.

In order to illustrate a method for inducing principally parallel axial motion across a bone fracture, FIG. 18B depicts a cross-sectional view of an embodiment for elastic fixation of a bone fracture subjected to axial loading, as may be the case in patients that start weight bearing of a fractured extremity that has been stabilized with bone plate 1801. In various embodiments, the load acting on bone segments 1826 and onto locking screws 1810 may induce elastic translation of receiving holes 1805 relative to bone plate 1801, which in turn may cause generally parallel motion between bone segments 1826 at bone fracture 1824. In this configuration, axial loading of bone segments 1826 may cause elastic deformation of elastic beam elements 1808, wherein slot segments 1832 located at the aspect of receiving hole 1805 facing fracture 1824 become narrower, while slot segments 1834 located at the receiving hole aspect facing away from fracture 1824 become wider.

Figure 19:
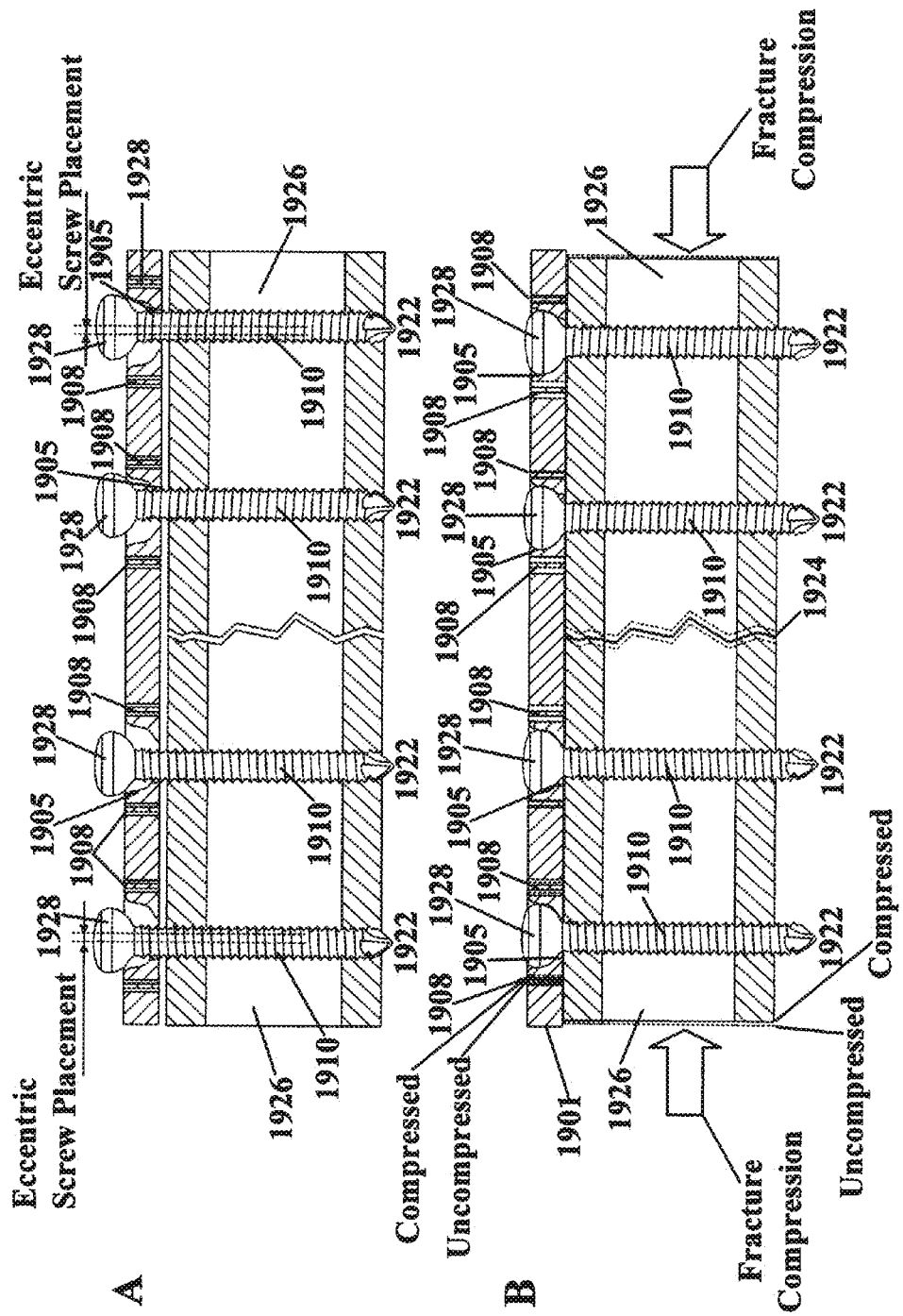
FIG. 19A illustrates a cross-sectional side view of a bone plate for elastic compression of a bone fracture, shown in functional association with non-locking bone screws for spanning a bone facture in a cylindrical bone, wherein bone screws are inserted in an eccentric manner, in accordance with various embodiments.
FIG. 19B illustrates a cross-sectional side view of a bone plate for elastic compression of a bone fracture, wherein tightening of eccentrically inserted bone screws induces elastic compression across a bone fracture by deformation of elastic beam elements that connect the plate holes to the plate member, in accordance with various embodiments.

In various other embodiments, FIG. 19A illustrates a cross-sectional side view of a bone plate for elastic compression of a bone fracture, shown in functional association with non-locking bone screws for spanning a bone facture in a cylindrical bone, wherein bone screws are inserted in an eccentric manner, and FIG. 19B illustrates a cross-sectional side view of a bone plate for elastic compression of a bone fracture, wherein tightening of eccentrically inserted bone screws induces elastic compression across a bone fracture by deformation of elastic beam elements that connect the plate holes to the plate member, both in accordance with various embodiments.

Thus, in order to illustrate a method for inducing elastic compression across a bone fracture, FIGS. 19A and 19B depict cross-sectional views of an embodiment of a bone plate 1901 applied to bridge and to elastically compress a fracture 1924 in a substantially cylindrical bone. FIG. 19A depicts bone screws 1910 being partially inserted through receiving holes 1905 into bone segments 1926. In various embodiments, screws 1910 may be inserted eccentrically in receiving holes 1905, at a small distance from the center-line 1922 of receiving hole 1905 in an opposite direction from fracture 1924. FIG. 19B depicts the embodiment in a cross-sectional view after complete insertion of screws 1910. Since screws 1910 were inserted eccentrically relative to receiving hole 1905, once screw heads 1928 are contacting bone plate 1901 during insertion, screws 1910 may be forced to translate toward the center of receiving holes 1905. This in turn causes bone segment 1926 attached to screws 1910 to translate relative to bone plate 1901 toward fracture 1924, thereby inducing compression across fracture 1924. Once fracture 1924 is fully compressed, any further translation may be accommodated by deformation of elastic beam elements 1908 connecting receiving holes 1905 to bone plate 1901. In embodiments, this elastic deformation may induce additional compressive forces at fracture 1924.

Figure 20:
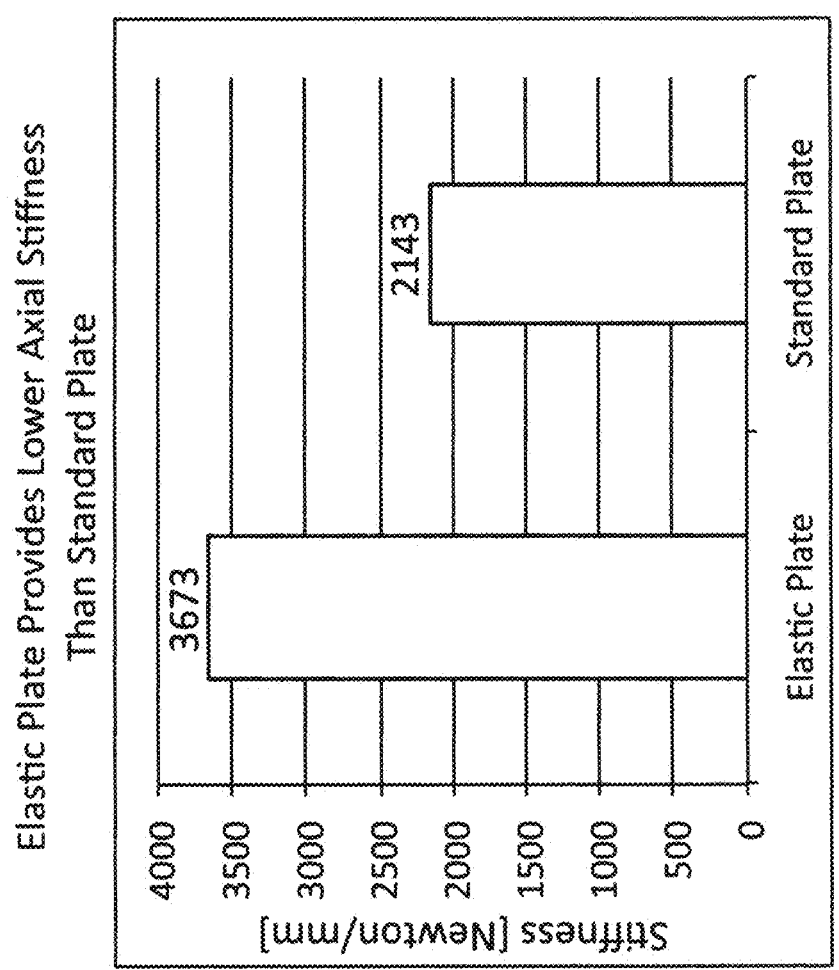
FIG. 20 is a graph comparing axial stiffness of a standard plate with that of a plate with spring elements ("S-Plate") in accordance with embodiments herein.

As illustrated in FIG. 20, the introduction of elastic elements in a bone plate as described elsewhere herein (referred to in FIG. 20 as an S-plate) may reduce axial stiffness of the plate as compared to a standard plate without the elastic elements. Notably, there is little to no impact on the bending stiffness of the plate due to the introduction of the elastic elements.

Thus, in some embodiments, having an opening with a major dimension in a transverse direction may effectively reduce the bending strength of bone plates, which may fail in bending. Thus in various embodiments, the flexible elements described herein may not have a major dimension extending in transverse direction. This orientation may cause the bone plate to retain a substantial amount of bending strength. As described elsewhere herein, it is desirable to maintain the bending strength of the construct while reducing the axial stiffness of plate, and additionally reducing stress at the screw hole(s) and in the construct as a whole. In various embodiments, stress at the screw hole(s) may cause undesirable or detrimental deformation of the hole(s).

In other embodiments, if the cantilever beam were located transversely 'in-line' with the screw hole, the transverse opening may extend over a substantial portion of the plate in order to derive flexibility, which in turn may reduce the bending strength of the plate. Thus, various embodiments disclosed herein employ a combination of two or more cantilever beams located above and below the screw hole (e.g., in the longitudinal plate direction), which may preserve bending strength of the plate.

In still other embodiments described herein, one or more pairs of cantilever beams may be employed, wherein the beams of each cantilever pair are located on opposite sides of the screw hole in longitudinal direction, rather than one cantilever beam element that extends in a principally transverse direction to either one or both sides of the screw hole (lug), depending if the screw hole is located offset from or located on the longitudinal plate midline, respectively.

Other embodiments disclosed herein use pairs of slots that extend through the plate edge, rather than a slot that defines the transverse opening and that surrounds the beam and lug element, wherein the slot remains within the plate surface and does not extend through the plate edge.

Still other embodiments include a set of slots per screw hole, wherein the set combines a central slot that partially surrounds the screw hole without extending through the plate edge with peripheral slots that penetrate through the longitudinal plate edge, rather than one continuous slot per screw hole, whereby the slot defines the transverse opening and surrounds the beam and lug element.

Various other embodiments disclosed herein employ a set of slots to form a principally S-shaped spring element having an upper and a lower cantilever element that is diagonally connected by a central segment that contains the screw hole, rather than a generally I-shaped cantilever beam, for instance. Still other embodiments described herein employ cantilever elements of a width that is substantially smaller than the plate thickness, rather than a cantilever element of a width that is larger than the plate thickness. This may ensure a desired bending direction of the cantilever beam within the plane of the plate rather than out of the plane of the plate.

It will be appreciated by those skilled in the art that changes could be made to the embodiments described above without departing from the broad inventive concept thereof. Specifically, the disclosed invention may be practiced for fixation of a bone plate to one side of a fracture only, whereby the corresponding side of a fractured bone may be applied to the one plate by alternative means for flexible or rigid fixation. It is understood, therefore, that this disclosure is not limited to the particular embodiments disclosed, but it is intended to cover modifications within the spirit and scope of the present disclosure as defined by the appended claims.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method for flexible plate fixation of a bone fracture, the method comprising:
   approximately aligning two or more fractured bone members;
   applying a bone plate across the fracture with a plurality of fixation elements that rigidly connect to receiving holes in the plate, each of the receiving holes including at least one surface projection for engagement with the fixation elements, wherein the bone plate comprises a plurality of flexible elements connecting the receiving holes to the plate, each of the flexible elements formed by one or more slots extending through the plate and at least partially surrounding a periphery of one of the receiving holes; and
   rigidly fixing the fixation elements to the receiving holes in the plate;
   wherein the flexible elements are configured to permit axial translation relative to the receiving holes within a plane parallel to an upper or lower plane of the bone plate, after the fixation elements have been rigidly fixed to the receiving holes in the plate; and
   wherein the flexible elements are configured to substantially prevent translation of the bone plate relative to the receiving holes in a direction substantially perpendicular to the upper or lower plane of the bone plate.

2. The method of claim 1, wherein the method permits principally longitudinal axial motion across a bone fracture.

3. A method of claim 1, wherein the method allows selective angulation of screws through angulation of the receiving hole with respect to the plate.

4. The method of claim 1, wherein the method permits substantially symmetric motion of the fracture gap.

5. The method of claim 1, wherein the method further comprises forming a plate resulting in principally longitudinal axial motion in a stiffness range of b 200-1200 N/mm.

6. The method of claim 1, wherein the flexible elements are formed integral to the bone plate.

7. The method of claim 1, wherein the flexible elements provide an elastic interface between the receiving holes and the bone plate.

8. The method of claim 1, wherein the surface projection is a thread.

9. The method of claim 1, wherein the one or more slots extend from an outer surface of the bone plate to a bone-facing surface of the bone plate.

10. The method of claim 9, wherein the one or more slots do not penetrate through a longitudinal edge of the bone plate.

11. A method of reducing stress concentrations at a screw-bone interface comprising:
   aligning two or more fractured bone members; and
   applying a bone plate across the fracture with a plurality of screws; thereby reducing stress concentrations at the screw-bone interface, wherein the bone plate comprises:
   an outer surface and a bone-facing surface;
   a plurality of fixation elements that connect to one or more receiving holes in the bone plate, each of the one or more receiving holes including at least one thread; and
   one or more slots at least partially circumscribing a periphery of one or more receiving holes and not penetrating through a longitudinal edge of the bone plate, wherein the one or more slots form a spring element, the spring element at least partially surrounding the receiving hole and permitting axial translation of the bone plate relative to the one or more receiving holes within a plane that is substantially parallel to an upper or lower surface of the bone plate, but substantially preventing motion of the bone plate relative to the one or more receiving holes in a direction that is substantially perpendicular to the upper or lower surface of the bone plate after the fixation elements have been rigidly fixed to the receiving holes in the plate.

12. A method of reducing stresses during loading by allowing principally longitudinal motion to increase duration of load attenuation, the method comprising:

aligning two or more fractured bone members defining a fracture; and applying a bone plate across the fracture with a plurality of screws, thereby reducing stress concentrations at a screw-bone interface, wherein the bone plate comprises:
an outer surface and a bone-facing surface;
a plurality of fixation elements that connect to one or more receiving holes in the bone plate, each of the one or more receiving holes including at least one thread; and
one or more slots extending through the plate from the outer surface to the bone-facing surface, the one or more slots at least partially circumscribing a periphery of one or more receiving holes and not penetrating through a longitudinal edge of the bone plate, wherein the one or more slots form a spring element, the spring element at least partially surrounding the receiving hole and permitting axial translation of the bone plate relative to the one or more receiving holes within a plane that is substantially parallel to an upper or lower surface of the bone plate, but substantially preventing motion of the bone plate relative to the one or more receiving holes in a direction that is substantially perpendicular to the upper or lower surface of the bone plate after the fixation elements have been rigidly fixed to the receiving holes in the plate.

* * * * *

UNITED STATES PATENT AND TRADEMARK OFFICE
CERTIFICATE OF CORRECTION

PATENT NO. : 8,992,583 B2
APPLICATION NO. : 13/554119
DATED : March 31, 2015
INVENTOR(S) : Bottlang et al.

Page 1 of 1

It is certified that error appears in the above-identified patent and that said Letters Patent is hereby corrected as shown below:

In the Claims

In column 16, line 29, in Claim 3, delete "A" and insert --The--, therefor

In column 16, line 36, in Claim 5, after "of", delete "b", therefor

In column 16, line 53, in Claim 11, delete "screws;" and insert --screws,--, therefor Signed and Sealed this
Twenty-eighth Day of July, 2015

Michelle K. Lee
*Director of the United States Patent and Trademark Office*